US012569690B2

(12) United States Patent
Prutchi et al.

(10) Patent No.: US 12,569,690 B2
(45) Date of Patent: Mar. 10, 2026

(54) CARDIAC CONTRACTILITY MODULATION FOR ATRIAL ARRHYTHMIA PATIENTS

(71) Applicant: Impulse Dynamics NV, Willemstad (CW)

(72) Inventors: David Prutchi, Voorhees, NJ (US); Simeon Ioannis Kedikoglou, Tallahassee, FL (US); Angela Connolly Stagg, Allendale, NJ (US); Tamir Ben David, Tel-Aviv (IL)

(73) Assignee: Impulse Dynamics NV, Willemstad (NL)

( * ) Notice: Subject to any disclaimer, the term of this patent is extended or adjusted under 35 U.S.C. 154(b) by 184 days.

(21) Appl. No.: 17/770,329

(22) PCT Filed: Oct. 22, 2020

(86) PCT No.: PCT/IB2020/059949
§ 371 (c)(1),
(2) Date: Apr. 20, 2022

(87) PCT Pub. No.: WO2021/079319
PCT Pub. Date: Apr. 29, 2021

(65) Prior Publication Data
US 2022/0387795 A1 Dec. 8, 2022

Related U.S. Application Data

(60) Provisional application No. 62/924,776, filed on Oct. 23, 2019, provisional application No. 62/924,782, (Continued)

(51) Int. Cl.
*A61N 1/362* (2006.01)
*A61N 1/365* (2006.01)

(52) U.S. Cl.
CPC ....... *A61N 1/36585* (2013.01); *A61N 1/3624* (2013.01); *A61N 1/3628* (2013.01); *A61N 1/36592* (2013.01)

(58) Field of Classification Search
CPC ........................... A61N 1/3624; A61N 1/3628
See application file for complete search history.

(56) References Cited

U.S. PATENT DOCUMENTS 4,554,922 A 11/1985 Prystowsky et al.
5,372,607 A 12/1994 Stone et al.
(Continued)

FOREIGN PATENT DOCUMENTS

CA 2459408 3/2003
CN 1787850 6/2006
(Continued)

OTHER PUBLICATIONS

Official Action Dated Jan. 17, 2024 from the US Patent and Trademark Office Re. U.S. Appl. No. 17/857,085. (11 pages).
(Continued)

*Primary Examiner* — William J Levicky

(57) ABSTRACT

A cardiac treatment device, including:
stimulation circuitry configured to generate a non-excitatory electrical signal which, when applied to ventricular tissue during a ventricular refractory period thereof improves a condition of heart failure in human patients;
atrial arrhythmia detection circuitry; and
decision circuitry which controls the stimulation circuitry to delivery said signal, also when said atrial arrhythmia detection circuitry detects an atrial arrhythmia.

32 Claims, 10 Drawing Sheets

Identify patient (802)

Determine AA status (804)

Determine HF status (806)

Determine PR status (808)

Determine suitability (810)

Determine initial settings (812)

Implant lead(s) (814)

Select electrodes (816)

Monitor (818)

Program/reprogram (820)

Related U.S. Application Data filed on Oct. 23, 2019, provisional application No. 63/001,343, filed on Mar. 29, 2020, provisional application No. 63/042,061, filed on Jun. 22, 2020.

(56) References Cited

U.S. PATENT DOCUMENTS

| | | | |
|---|---|---|---|
| 6,233,487 | B1 | 5/2001 | Mika et al. |
| 6,263,242 | B1 | 7/2001 | Mika et al. |
| 6,370,430 | B1 | 4/2002 | Mika et al. |
| 6,480,737 | B1 | 11/2002 | Policker et al. |
| 6,597,952 | B1 | 7/2003 | Mika et al. |
| 6,725,093 | B1 | 4/2004 | Ben-Haim et al. |
| 6,993,385 | B1 | 1/2006 | Routh et al. |
| 7,027,863 | B1 | 4/2006 | Prutchi et al. |
| 7,519,426 | B1 | 4/2009 | Koh et al. |
| 7,634,310 | B2 | 12/2009 | Lee et al. |
| 7,953,481 | B1 | 5/2011 | Shemer et al. |
| 7,991,469 | B2 | 8/2011 | Schwartz et al. |
| 8,634,910 | B2 | 1/2014 | Stahmann |
| 8,977,353 | B2 | 3/2015 | Rousso et al. |
| 9,713,723 | B2 | 7/2017 | Shemer et al. |
| 10,207,110 | B1 | 2/2019 | Gelfand et al. |
| 2003/0036777 | A1 | 2/2003 | Sheth et al. |
| 2004/0127804 | A1 | 7/2004 | Hatlesad et al. |
| 2005/0039745 | A1 | 2/2005 | Stahmann et al. |
| 2005/0085867 | A1 | 4/2005 | Tehrani et al. |
| 2005/0090871 | A1 | 4/2005 | Cho et al. |
| 2006/0100668 | A1 | 5/2006 | Ben-David et al. |
| 2006/0224190 | A1 | 10/2006 | Gill et al. |
| 2007/0060962 | A1* | 3/2007 | Pappone ............ A61N 1/36843 607/9 |
| 2008/0021336 | A1 | 1/2008 | Dobak, III |
| 2008/0103532 | A1* | 5/2008 | Armstrong ........... A61N 1/3605 607/2 |
| 2008/0114411 | A1 | 5/2008 | Lian et al. |
| 2008/0275520 | A1 | 11/2008 | Hopper et al. |
| 2009/0030471 | A1 | 1/2009 | Rousso et al. |
| 2009/0062882 | A1 | 3/2009 | Zhang et al. |
| 2009/0248101 | A1 | 10/2009 | Anker |
| 2009/0287103 | A1 | 11/2009 | Pillai |
| 2010/0069977 | A1 | 3/2010 | Stahmann |
| 2010/0069985 | A1* | 3/2010 | Stahmann .......... A61N 1/36185 607/9 |
| 2010/0087892 | A1 | 4/2010 | Stubbs et al. |
| 2010/0248288 | A1 | 9/2010 | Iless et al. |
| 2010/0305647 | A1 | 12/2010 | McCabe et al. |
| 2011/0152956 | A1 | 6/2011 | Hincapie-Ordonez et al. |
| 2013/0006319 | A1* | 1/2013 | Doerr ................... A61N 1/3684 607/18 |
| 2013/0138006 | A1* | 5/2013 | Bornzin ................ A61B 5/283 600/509 |
| 2013/0218222 | A1 | 8/2013 | Doerr |
| 2016/0045732 | A1 | 2/2016 | Grenz et al. |
| 2017/0245794 | A1 | 8/2017 | Sharma et al. |
| 2017/0348524 | A1 | 12/2017 | Matos |
| 2018/0214698 | A1 | 8/2018 | Cuchiara |
| 2019/0060632 | A1 | 2/2019 | Asirvatham et al. |
| 2019/0329043 | A1 | 10/2019 | Sharma |
| 2019/0329052 | A1 | 10/2019 | Kim et al. |
| 2022/0379120 | A1 | 12/2022 | Prutchi et al. |
| 2022/0387790 | A1 | 12/2022 | Prutchi et al. |
| 2023/0001204 | A1 | 1/2023 | Prutchi et al. |
| 2023/0173280 | A1 | 6/2023 | Prutchi et al. |

FOREIGN PATENT DOCUMENTS

| | | |
|---|---|---|
| CN | 1882296 | 12/2006 |
| CN | 101827629 | 9/2010 |
| CN | 104321107 | 1/2015 |
| CN | 107261324 | 10/2017 |
| EP | 0334675 | 9/1989 |
| EP | 0600631 | 6/1994 |
| EP | 0910429 | 4/1999 |
| EP | 2659931 | 11/2013 |
| JP | 2007-503286 | 2/2007 |
| JP | 2008-532630 | 8/2008 |
| JP | 2010-104750 | 5/2010 |
| JP | 2011-502552 | 1/2011 |
| JP | 2012-502729 | 2/2012 |
| JP | 2012-504468 | 2/2012 |
| JP | 2015-503397 | 2/2015 |
| WO | WO 2004/080533 | 9/2004 |
| WO | WO 2010/039877 | 4/2010 |
| WO | WO 2021/079316 | 4/2021 |
| WO | WO 2021/079318 | 4/2021 |
| WO | WO 2021/079319 | 4/2021 |
| WO | WO 2021/198755 | 10/2021 |

OTHER PUBLICATIONS

International Preliminary Report on Patentability Dated May 5, 2022 From the International Bureau of WIPO Re. Application No. PCT/IB2020/059943. (8 Pages).

International Preliminary Report on Patentability Dated May 5, 2022 From the International Bureau of WIPO Re. Application No. PCT/IB2020/059947. (10 Pages).

International Preliminary Report on Patentability Dated May 5, 2022 From the International Bureau of WIPO Re. Application No. PCT/IB2020/059949. (10 Pages).

International Preliminary Report on Patentability Dated Jul. 21, 2022 From the International Preliminary Examining Authority Re. Application No. PCT/IB2020/059944. (21 Pages).

Communication Pursuant to Article 94(3) EPC Dated Dec. 22, 2023 From the European Patent Office Re. Application No. 20801017.3 (4 Pages).

International Search Report and the Written Opinion Dated Feb. 4, 2021 From the International Searching Authority Re. Application No. PCT/IB2020/059949. (14 Pages).

International Search Report and the Written Opinion Dated Aug. 12, 2021 From the International Searching Authority Re. Application No. PCT/IB2020/059947. (16 Pages).

International Search Report and the Written Opinion Dated Jan. 14, 2021 From the International Searching Authority Re. Application No. PCT/IB2020/059943. (17 Pages).

International Search Report and the Written Opinion Dated Aug. 20, 2021 From the International Searching Authority Re. Application No. PCT/IB2020/059944. (18 Pages).

Invitation to Pay Additional Fees, Communication Relating to the Result of the Partial International Search and the Provisional Opinion Dated Apr. 20, 2021 From the International Searching Authority Re. Application No. PCT/IB2020/059944. (9 Pages).

Invitation to Pay Additional Fees, Communication Relating to the Result of the Partial International Search and the Provisional Opinion Dated Apr. 26, 2021 From the International Searching Authority Re. Application No. PCT/IB2020/059947. (9 Pages).

Written Opinion Dated Mar. 15, 2022 From the International Searching Authority Re. Application No. PCT/IB2020/059944. (9 Pages).

Abi-Samra et al. "Cardiac Contractility Modulation: A Novel Approach for the Treatment of Heart Failure", Heart Fail Reviews 21:645-660, Jul. 9, 2016.

Abraham et al. "A Randomized Controlled Trial to Evaluate the Safety and Efficacy of Cardiac Contractility Modulation in Patients With Moderately Reduced Left Ventricular Ejection Fraction and A Narrow QRS Duration: Study Rationale and Design", Journal of Cardiac Failure, 21(1): 16-23, Jan. 2015.

Abraham et al. "A Randomized Controlled Trial to Evaluate the Safety and Efficacy of Cardiac Contractility Modulation", Journal of the American College of Cardiology, JACC: Heart Failure, 6(10): 874-883, Published Online May 10, 2018.

Abraham et al. "Subgroup Analysis of A Randomized Controlled Trial Evaluating the Safety and Efficacy of Cardiac Contractility Modulation in Advanced Heart Failure", Journal of Cardiac Failure, 17(9): 710-717, Published Online Jun. 22, 2011.

Anker et al. "Cardiac Contractility Modulation Improves Long-Term Survival and Hospitalizations in Heart Failure With Reduced

(56) References Cited

OTHER PUBLICATIONS

Ejection Fraction", European Journal of Heart Failure, 21(9): 1103-1113, Published Online Jan. 16, 2019.

Borggrefe et al. "Randomized, Double Blind Study of Non-Excitatory, Cardiac Contractility Modulation Electrical Impulses for Symptomatic Heart Failure", European Heart Journal, 29(8): 1019-1028, Published Online Feb. 12, 2008.

Giallauria et al. "Effects of Cardiac Contractility Modulation by Non-Excitatory Electrical Simulation on Exercise Capacity and Quality of Life: An Individual Patient's Data Meta-Analysis of Randomized Controlled Trials", International Journal of Cardiology, XP028880522, 175(2): 352-357, Available Online Jun. 19, 2014.

Ibrahim et al. "Power Prior Distributions for Regression Models", Statistical Science, 15(1): 46-60, Feb. 2000.

Kadish et al. "A Randomized Controlled Trial Evaluating the Safety and Efficacy of Cardiac Contractility Modulation in Advanced Heart Failure", American Heart Journal, 161(2): 329-337, Feb. 2011.

Kuschyk et al. "Efficacy and Survival in Patients With Cardiac Contractility Modulation: Long-Term Single Center Experience in 81 Patients", International Journal of Cardiology, 183: 76-81, Available Online Jan. 20, 2015.

Liu et al. "Improvement of Long-Term Survival by Cardiac Contractility Modulation in Heart Failure Patients: A Case-Control Study", International Journal of Cardiology, 206: 122-126, Available On line Jan. 6, 2016.

Lyon et al. "Cardiac Contractility Modulation Therapy in Advanced Systolic Heart Failure", Nature Reviews Cardiology, XP0557621686, 10(10): 584-598, Advance Online Publication Aug. 13, 2013.

Mando et al. "Outcomes of Cardiac Contractility Modulation: A Systemic Review and Meta-Analysis of Randomized Clinical Trials", Cardiovascular Therapeutics, 2019(Art.ID 9769724): 1-10, Jun. 17, 2019.

Mueller et al. "Clinical Effects of Long-Term Cardiac Contractility Modulation (CCM) in Subjects With Heart Failure Caused by Left Ventricular Systolic Dysfunction", Clinical Research of Cardiology, 106(11): 893-904, Published Online Jul. 6, 2017.

Neelagaru et al. "Nonexcitatory, Cardiac Contractility Modulation Electrical Impulses: Feasibility Study for Advanced Heart Failure in Patients With Normal QRS Duration", Heart Rythm, 3(10): 1140-1147, Published Online Jul. 8, 2006.

Schoene ct al. "Cardiac Contractility Modulation Provides Improved Ventilatory Efficiency and Reduces Oscillatory Breathing Pattern", European Heart Journal, Poster Session 4: Advanced Heart Failure, 40(Suppl.1): 2133: # P3523, Oct. 21, 2019.

Schuirmann "Pharmacometrics: A Comparison of the Two One-Sided Tests Procedure and the Power Approach for Assessing the Equivalence of Average Bioavailability", Journal of Pharmacokinetics and Biopharmaceutics, 15(6): 657-680, Dec. 1987.

Tint et al. "New Generation Cardiac Contractility Modulation Device—Filling the Gap in Heart Failure Treatment", Journal of Clinical Medicine, 8(5): 588-1-588-10, Apr. 29, 2019.

Tschoepe et al. "Cardiac Contractility Modulation: Mechanisms of Action in Heart Failure with Reduced Ejection Fraction and Beyond", European Journal of Heart Failure, 21(1):14-20, Nov. 28, 2018.

Uskach et al. "Possibilities and Perspectives of Using Cardiac Contractility Modulation in Patients With Chronic Heart Failure and Atrial Fibrillation", Kardiologiia, 59(2S): 4-14, 2019 & English Abstract.

Wang et al. "Meta-Analysis of the Incidence of Lead Dislodgement With Conventional and Leadless Pacemaker Systems", Pacing and Clinical Electrophysiology, PACE, 41(10): 1365-1371, Published Online Aug. 27, 2018.

Yu et al. "Impact of Cardiac Contractility Modulation on Left Ventricular Global and Regional Function and Remodeling", Journal of the American College of Cardiology, JACC: Cardiovascular Imaging, 2(12): 1341-1349, Dec. 2009.

Official Action Dated Sep. 8, 2023 from the US Patent and Trademark Office Re. U.S. Appl. No. 17/857,085. (24 pages).

Eisman et al. "Pulmonary Capillary Wedge Pressure Patterns During Exercice Predict Exercise Capacity and Incident Heart Failure", Circulation: Heart Failure, 11(5): 1-9, May 2018.

Meluzin et al. "Improvement in The Prediction of Exercise-Induced Elevation of Left Ventricular Filling Pressure in Patients With Normal Left Ventricular Ejection Fraction", Echocardiography, 34(1): 78-86, Oct. 25, 2016. Abstract.

Official Action Dated Aug. 5, 2024 from the US Patent and Trademark Office Re. U.S. Appl. No. 17/857,085. (21 pages).

Cleveland Clinic "Hypertrophic Cardiomyopathy", Cleveland Clinic, Retrieved Online, pp. 1-2, 2021.

Meluzin et al. "Noninvasive Prediction of the Exercise-Induced Elevation in Left Ventricular Filling Pressure in Post-Heart Transplant Patients With Normal Left Ventricular Ejection Fraction", Clinical Cardiology, 18(2): 63-72, 2013.

Notice of Reason(s) for Rejection Dated Jun. 11, 2024 From the Japan Patent Office Re. Application No. 2022-523998 and Its Translation Into English. (10 Pages).

Notice of Reason(s) for Rejection Dated Jun. 6, 2024 From the Japan Patent Office Re. Application No. 2022-523513 and Its Translation Into English. (12 Pages).

Notice of Reason(s) for Rejection Dated May 28, 2024 From the Japan Patent Office Re. Application No. 2022-523514 and Its Translation Into English. (14 Pages).

Additional Search Fees Due under Rule 164(2)(a) EPC Dated Feb. 26, 2025 From the European Patent Office Re. Application No. 20803263.1 (5 pages).

Notice of Reason(s) for Rejection Dated Mar. 4, 2025 From the Japan Patent Office Re. Application No. 2022-523514 and Its Translation Into English. (12 Pages).

Notice of Reason(s) for Rejection Dated Feb. 12, 2025 From the Japan Patent Office Re. Application No. 2022-523998 and Its Translation Into English. (9 Pages).

Notification of Office Action and Search Report Dated Apr. 1, 2025 From the State Intellectual Property Office of the People's Republic of China Re. Application No. 202080089348.6 and Its Machine Translation of Office Action into English. (10 Pages).

Notification of Office Action and Search Report Dated Mar. 19, 2025 From the State Intellectual Property Office of the People's Republic of China Re. Application No. 202080088570.4 and its Translation of the Office Action into English. (30 Pages).

Notification of Office Action and Search report Dated Mar. 21, 2025 From the State Intellectual Property Office of the People's Republic of China Re. Application No. 202080090192.3 and Its Translation in English (18 Pages).

Notification of Office Action and Search Report Dated Mar. 26, 2025 From the State Intellectual Property Office of the People's Republic of China Re. Application No. 202080101268.8 and Its Machine Translation of Office Action into English. (26 Pages).

Official Action Dated Feb. 6, 2025 from the US Patent and Trademark Office Re. U.S. Appl. No. 17/911,676. (48 pages).

Oliver et al. "Anatomy, Thorax, Phrenic Nerves", Europe PMC, Search life-sciences literature, Study Guide from StatPearls Publishing, Treasure Island (FL), PMID: 30020697, Jul. 19, 2018. dowloaded from https://europepmc.org/article/nbk/nbk513325.

Pre Appeal Examination Dated Aug. 18, 2025 From the Japan Patent Office Re. Application No. 2022-523514 and Its Translation Into English. (4 Pages).

Interview Summary Dated Nov. 12, 2024 from the US Patent and Trademark Office Re. U.S. Appl. No. 17/857,085. (8 pages).

Notice of Reasons for Rejection Dated Dec. 3, 2024 From the Japan Patent Office Re. Application No. 2022-523513 and Its Translation into English. (10 Pages).

Restriction Official Action Dated Dec. 30, 2024 from the US Patent and Trademark Office Re. U.S. Appl. No. 17/770,318. (5 pages).

Restriction Official Action Dated Jan. 6, 2025 from the US Patent and Trademark Office Re. U.S. Appl. No. 17/770,707. (12 pages).

* cited by examiner

CARDIAC CONTRACTILITY MODULATION FOR ATRIAL ARRHYTHMIA PATIENTS

RELATED APPLICATIONS

This application is a National Phase of PCT Patent Application No. PCT/IB2020/059949 having International filing date of Oct. 22, 2020, which claims the benefit of priority under 35 USC § 119(e) of U.S. Provisional Patent Application Nos. 63/042,061 filed on Jun. 22, 2020, 62/924, 776 filed on Oct. 23, 2019, 63/001,343 filed on Mar. 29, 2020, and 62/924,782 filed on Oct. 23, 2019.

PCT Patent Application No. PCT/IB2020/059949 is part of a co-filing of the following PCT applications, all filed on Oct. 22, 2020 and by the same applicant, Impulse Dynamics NV:

PCT Patent Application No. PCT/IB2020/059943 titled "INCREASING PEAK VO2 IN PATIENTS WITH HF USING CARDIAC CONTRACTILITY MODULATION STIMULATION";

PCT Patent Application No. PCT/IB2020/059947 titled "METHODS FOR PLANNING AND DELIVERING CARDIAC ELECTRICAL STIMULATION"; and PCT Patent Application No. PCT/IB2020/059944 titled "CARDIAC CONTRACTILITY MODULATION IN ASSOCIATION WITH RESPIRATION".

The contents of the above applications are all incorporated by reference as if fully set forth herein in their entirety.

FIELD AND BACKGROUND OF THE INVENTION

The present invention, in some embodiments thereof, relates to providing electrical stimulation, for example, non-excitatory stimulation, for example cardiac contractility modulation stimulation (C2MS) therapy, to patients with an atrial arrhythmia (AA), for example, atrial fibrillation (AF), for example, to increase cardiac output, to treat and/or prevent AF, AF symptoms and/or other diseases.

U.S. Pat. No. 9,713,723B2 describes using a refractory-period signal from the right ventricle to affect a left ventricle, "A method is provided for use with a human subject. The method includes accessing a cardiac site via a vena cava of the subject, and alleviating heart failure of the subject by applying to the cardiac site, during a refractory period of the site, a refractory-period signal that affects the left ventricle of the subject's heart. Other embodiments are also described."

U.S. Pat. No. 6,480,737 teaches using a method of arrhythmia detection based on ventricular leads, in which is disclosed "Apparatus for applying a non-excitatory signal to a heart, comprising: at least one electrode, a power source, a wide-field ECG sensor that receives a wide-field ECG signal containing contributions from non-local sized portions of the heart, a controller for selectively electrifying said at least one electrode with a non-excitatory signal from said power source, and a safety filter that inhibits said electrifying responsive to said wide-field ECG signal" and "In an exemplary embodiment of the invention, the wide field ECG sensor covers part of the right ventricle and part of the left ventricle (e.g., near the apex) and the temporal portion used for the match is between a right ventricle sensing event and a latest reasonable left ventricle ETC application event. When the right ventricle is paced, the trace may start slightly after the pacing event. Optionally, the template also includes portions from after the application of the ETC signal."

U.S. Pat. No. 9,713,723B2 discusses using a type of C2MS therapy to reduce prevalence of arrhythmia, apparently ventricular arrhythmia, in claim 1: "A method of applying a plurality of cardiac contractility modulating electrical signals to the heart, the method comprising: calculating a level of arrhythmia prevalence by counting a plurality of arrhythmic episodes in said heart during a given period; comparing between said level of arrhythmia prevalence and a value representing a level of arrhythmia prevalence of arrhythmia to be treated; and applying, in response to an outcome of said comparing, one or more of said plurality of cardiac contractility modulating electrical signals to said heart for reducing said level of arrhythmia prevalence, wherein said cardiac contractility modulating electrical signals are capable of increasing contractility of cardiac muscle cells of the heart."

U.S. Pat. No. 8,977,353B2 discusses short and long term effects, in claim 1: "A method of modifying cardiac tissue behavior at a first location by application of an electric field to cardiac tissue at a second location, comprising: determining a desired non-acute modification of protein activity and/or gene activity of cardiac tissue at said first location; selecting electric field parameters including one or more of the second location, the duration of application of the field and the power level of the field having an expected effect of producing said desired non-acute modification of said protein activity and/or gene activity at said first location, but without causing a significant acute effect at the first location; applying an electric field having the selected parameters to cardiac tissue at said second location to produce said selected non-acute modification at the first location, wherein said first location is sufficiently remote from said second location that a significant acute effect at the first location does not occur."

In the 2019 FDA approval of the Impulse Dynamics Optimizer® device using C2MS, permanent or persistent long-standing atrial fibrillation or flutter is listed as a contraindication and precaution, AF is considered a counter-indication for application of C2MS.

The paper "Cardiac contractility modulation: mechanisms of action in heart failure with reduced ejection fraction and beyond" by C. Tschope et al, European Journal of Heart Failure (2018), doi:10.1002/ejhf.1349 describes various possible mechanisms for operation of C2MS.

U.S. Pat. No. 4,554,922, apparently suggests that electrical signals applied in the relative refractory period extend the refractory period and make tissue less pro-arrhythmic.

The disclosures of all of the above documents are incorporated herein by reference.

SUMMARY OF THE INVENTION

Following is a non-exclusive list including some examples of embodiments of the invention. The invention also includes embodiments which include fewer than all the features in an example and embodiments using features from multiple examples, also if not expressly listed below.

Example 1. A cardiac treatment device, comprising:

stimulation circuitry configured to generate a non-excitatory electrical signal which, when applied to ventricular tissue during a ventricular refractory period thereof improves a condition of heart failure in human patients;

atrial arrhythmia detection circuitry; and decision circuitry which controls the stimulation circuitry to delivery said signal, also when said atrial arrhythmia detection circuitry detects an atrial arrhythmia.

Example 2. A device according to example 1, wherein said decision circuitry modifies at least one parameter of said signal in response to a detection of said atrial arrhythmia.

Example 3. A device according to example 2, wherein said modification comprises increasing a range of tissue stimulated by said signal.

Example 4. A device according to any of examples 1-3, wherein said decision circuitry is configured to avoid said delivery if a ventricular arrhythmia is detected.

Example 5. A device according to any of examples 1-4, wherein said decision circuitry is configured to allow said delivery if a supra-ventricular arrhythmia is detected.

Example 6. A device according to any of examples 1-5, wherein said device includes a memory with an indication of a dosage of said signal to be applied and a time duration of application and wherein said decision circuitry is configured to modify an actual duration of signal application according to an actual delivery of signals.

Example 7. A device according to any of examples 1-6, wherein said device includes a logger configured to record an effect of said applying on said detected atrial arrhythmia.

Example 8. A device according to any of examples 1-7, wherein said device is configured to apply said signal also during a non-refractory time in an atria of said patient.

Example 9. A device according to any of examples 1-8, wherein said device has no atrial leads.

Example 10. A device according to any of examples 1-8, wherein said device has no ventricular stimulation leads.

Example 11. A device according to any of examples 1-10, wherein said device includes pacing circuitry and wherein said decision circuitry is programmable to selectively prefer applying a non-excitatory signal over applying an increase in pacing in cases of increased cardiac demand.

Example 12. A device according to example 11, wherein said selective preference is in response to a cardiac parameter sensed by said device.

Example 13. A device according to any of examples 1-12, wherein said decision circuitry defines a prohibition window of a number of beats not to apply said signal, after an arrhythmia is detected and wherein said window is one or zero.

Example 14. A device according to any of examples 1-13, wherein said atrial arrhythmia detection circuitry detects atrial arrhythmia from signals measured by one or more ventricular leads.

Example 15. A method of planning treatment for a patient, comprising:

(a) identifying that a patient has an atrial arrhythmia or a risk to develop thereof; and (b) in response to said identifying, planning a treatment schedule for the patient with an implanted device that generates a non-excitatory electrical signal which, when applied to ventricular tissue during a ventricular refractory period thereof improves a condition of heart failure in human patients.

Example 16. A method according to example 15, wherein said planning comprises programming said device to apply said signal also during atrial arrhythmia.

Example 17. A method according to example 15, comprising selecting said patient and performing said planning with a goal of improving a symptom of said atrial arrhythmia by said treating.

Example 18. A method according to example 16 or example 17, wherein said improving comprises preventing abnormal ventricular activation by said atrial arrhythmia.

Example 19. A method according to any of examples 16-18, wherein said improving comprising reducing said atrial arrhythmia.

Example 20. A method according to any of examples 15-19, wherein said atrial arrhythmia comprises episodic AF.

Example 21. A method according to any of examples 15-20, wherein said planning comprises planning to apply said non-excitatory signal within 20 mm from a ventricular septum.

Example 22. A method according to any of examples 15-20, wherein said planning comprises planning to apply said non-excitatory signal within an atrium of the heart.

Example 23. A method according to any of examples 15-22, wherein said planning comprises selecting a power level and an application location to stimulate cardiac tissue in both an atria and a ventricle.

Example 24. A method according to any of examples 15-23, wherein said identifying comprises selecting for treatment patients with episodic AF.

Example 25. A method according to any of examples 15-23, wherein said identifying comprises selecting for treatment patients at risk of developing an AA, above 20% in the next year.

Example 26. A method according to any of examples 15-24, wherein said identifying comprises selecting for treatment patients with chronic AF.

Example 27. A method according to any of examples 15-26, wherein said identifying comprises selecting for treatment patients with heart failure of NYAH class II or class III.

Example 28. A method according to any of examples 15-26, wherein said identifying comprises selecting for treatment patients with heart failure without symptoms at rest.

Example 29. A method according to any of examples 15-26, wherein said identifying comprises selecting for treatment patients with heart failure at NYAH class IV.

Example 30. A method according to any of examples 15-27, wherein said identifying comprises selecting for treatment patients having a potential for increase in oxygenated oxygen flow, cardiac output permitting, of at least 30%.

Example 31. A method according to any of examples 15-28, wherein said identifying comprises selecting for treatment patients where at least 50% of beats are treatable using a device used for applying treatment.

Example 32. A method according to any of examples 15-31, wherein said planning comprises setting up device parameters to apply said signal to above 20,000 treated beats per day, on the average for a month.

Example 33. A method according to any of examples 15-32, wherein said planning comprises planning to treat using one or more application parameters and wherein said one or more application parameters comprises which of several leads to use.

Example 34. A method according to any of examples 15-33, wherein said planning comprises planning with a goal to improve VO2 max in said patient.

Example 35. A method according to any of examples 15-34, wherein said planning comprises planning with a goal to reduce AF episodes in said patient.

Example 36. A method according to any of examples 15-35, wherein said planning comprises programming the device to apply said signal even at beats and at times when the signal is excitatory for an atria.

Example 37. A method according to any of examples 15-36, wherein said planning comprises programming the device to applying said signal during a portion of the ventricular refractory period late enough so that said refractory period is extended.

Example 38. A method according to any of examples 15-36, wherein said planning comprises programming the device to apply said signal also during a time between 40 and 100 ms from a local activation time.

Example 39. A method of treating patients, comprising:

(a) identifying that a patient has a cardiac dysfunction comprising an atrial arrhythmia or a reduced cardiac output and an additional cardiac dysfunction; and (b) in response to said identifying, planning a treatment schedule for the patient with an implanted device that generates a non-excitatory electrical signal which, when applied to ventricular tissue improves heart failure in human patients said applying improving both said dysfunctions.

Example 40. A method according to example 39, wherein said improving comprises improving two dysfunction chambers using a same applied signal.

As can be appreciated, in some embodiments, treatment is applied according to the plan.

Example 41. A method of treating patients, comprising planning to apply a C2MS signal to a patient having an atrial arrhythmia and reduced cardiac output, at a time when said atrial arrhythmia is active.

Example 42. A method of treating patients, comprising planning to a C2MS signal to a patient having a potential for atrial arrhythmia and thereby reducing a probability of an atrial arrhythmia occurring in a next hour by at least 10%. Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as controlling cardiac stimulation equipment and/or processing cardiac signals in real time, might be expected to use completely different methods, e.g., making use of expert knowledge and/or the pattern recognition capabilities of the human brain, which would be vastly more efficient than manually going through the steps of the methods described herein, however, they can probably not work in the time scales needed.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
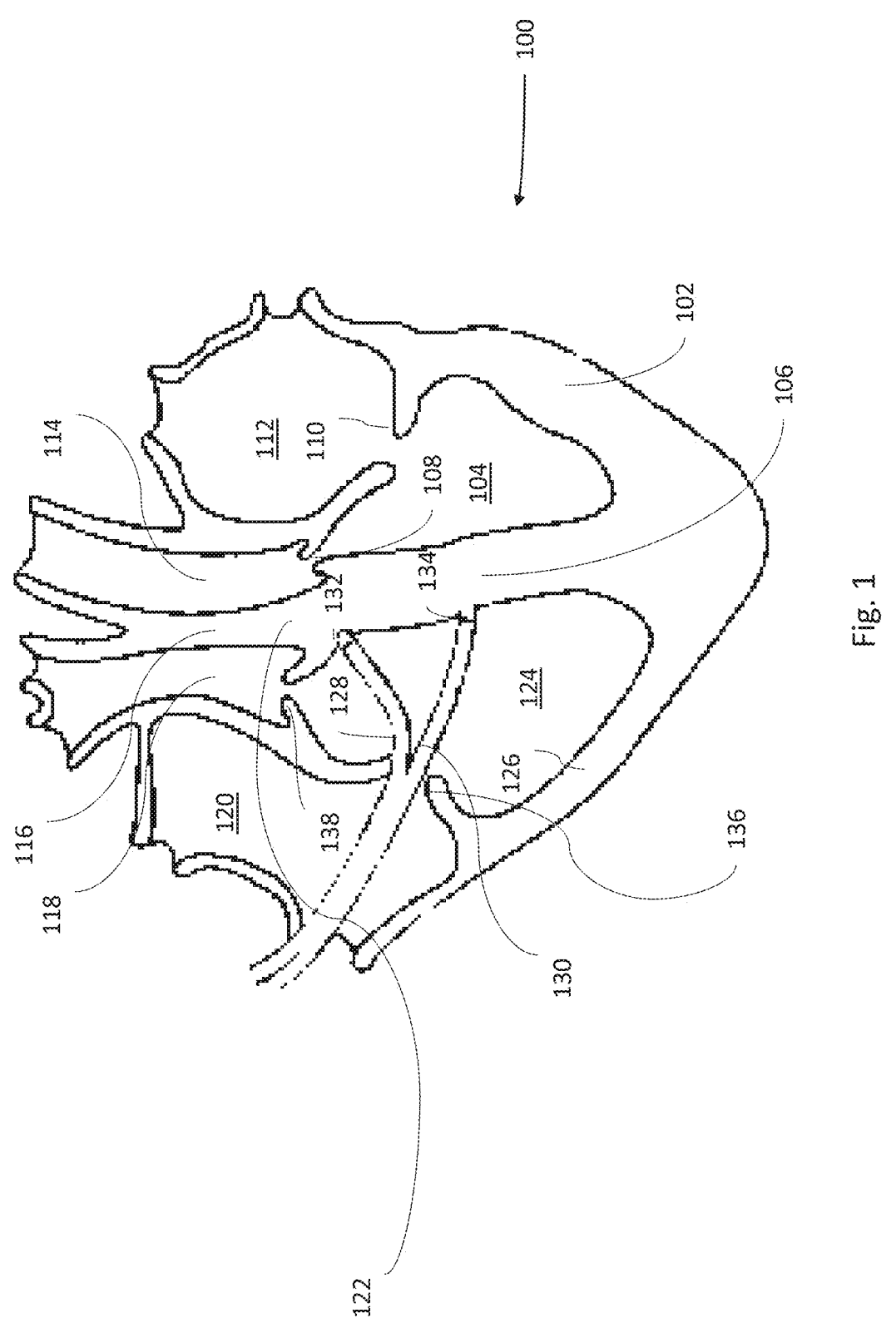
FIG. 1 is a schematic showing of a heart, showing various tissues and electrode/lead locations in accordance with some embodiments of the invention.

The present invention, in some embodiments thereof, relates to providing electrical stimulation, for example, non-excitatory stimulation, for example cardiac contractility modulation therapy, to patients with an atrial arrhythmia (AA), for example, atrial fibrillation (AF), for example, to increase cardiac output, to treat and/or prevent AF, AF symptoms and/or other diseases.

A broad aspect of some embodiments of the invention relates to planning for and/or treating patients with atrial arrhythmia. While atrial arrhythmia may have been previously considered a counter indication to applying C2MS therapy, inventors have found that C2MS can not only be safely applied in AF patients, such therapy appears to be useful as well. In some embodiments of the invention, a patient is treated, in general in spite of an AA diagnosis. Optionally or additionally, a patient is treated during an AA event. In some embodiments, such AA event is detected and does not stop (or, in some embodiments, triggers and/or otherwise modifies therapy). In some embodiments of the invention, such AA event is not detected, or is detected and ignored during application of therapy.

A broad aspect of some embodiments of the invention relates to using a strong non-excitatory signal applied to the heart to provide two or more different therapeutic effects with a same signal. Optionally one or more signal application parameters is optimized for such multiple desired effects. In some embodiments, such effects include both increasing cardiac contractility and improving an arrhythmic condition.

An aspect of some embodiments of the invention relates to treating patients (and/or generating treatment plan for such patients) having an atrial arrhythmia with a cardiac contractility modulating stimulation (C2MS) signal, for example, a non-excitatory signal applied to the heart during a relative and/or absolute refractory period of the heart. In some embodiments of the invention, the signal is selected to increase the contractility of a cardiac ventricle when the electric field of the signal stimulates such ventricular tissue, for example, the left ventricle, the right ventricle and/or a ventricular septum. In some embodiments of the invention, contractility modulation is provided by phosphorylation of phospholamban caused by the signal. In some embodiments of the invention, contractility modulation is caused by a change in protein transcription and/or mRNA creation caused by the signal, optionally in the form of reversal of a fetal gene program. The term "C2MS" is used herein, unless otherwise noted, as a general placeholder for all such signals. It is noted that in some embodiments the C2MS signal may be excitatory to tissue other than that to which it is applied. Various mechanisms by which C2MS signals may operate are described, for example in "Cardiac contractility modulation: mechanisms of action in heart failure with reduced ejection fraction and beyond" by C. Tschope et al, European Journal of Heart Failure (2018), doi:10.1002/ejhf.1349, the disclosure of which is incorporated herein by reference, and may serve to guide in selecting signal application parameters in order to utilize and/or comply with one or more of these mechanisms.

It is noted that patients without an AA may also be selected for treatment and/or that selection for treatment may optionally ignore an AA status or risk of the patient.

In some embodiments of the invention, patients are selected for treatment based on them having a co-morbidities of an atrial arrhythmia, for example, atrial flutter, paroxysmal AF, episodic AF and/or chronic AF, atrial tachycardia (AT) and/or based on an expectation of such arrhythmia developing. While some of the examples below focus on atrial fibrillation, it is noted that they may be usefully applied also for other atrial arrhythmia.

In some embodiments of the invention, patients are selected for treatment without a particular treatment goal. In others, such a treatment goal is selected, for example, based on expected results (e.g., improvement of NYHA functional class by at least 1 in over 50%, 60%, 70%, 80% or intermediate percentages of the cases).

In some embodiments of the invention, patients are selected based on a desire (and/or potential) to increase NYHA class by at least 0.5, 0.75, 1, 1.5 or intermediate or greater number of classes. In some embodiments of the invention, patients are selected if they have class III and/or class IVa heart failure.

In some embodiments of the invention, patients are selected based on a desire (and/or potential) to increase Peak VO2 of the patient, for example, by between 5 and 300%, for example, by between 10 and 50%. In some embodiments of the invention, the Peak VO2 is desired to be increased by between 1 and 10 ml O2/min/kg, for example, between 3 and 7 ml O2/min/kg. Optionally, the patients are selected which have an existing Peak VO2 between 5 and 25 ml O2/min/kg, for example, between 9 and 20 ml O2/min/kg. Optionally, this excludes some patients, for example, patients having no or reduced respiratory reserve (e.g., no or reduced ability to increase pulmonary throughput).

In some embodiments of the invention, the dosage of C2MS therapy is selected based on a desired amount of improvement in Peak VO2, for example, reduced dosage (fewer beats per day, fewer hours a day and/or less tissue directly stimulated) for patients where a lesser amount of improvement in Peak VO2 is desired, or to tradeoff issues relating to treating with C2MS with increased clinical health provided by C2MS. In one example, less C2MS is applied if the patient has a lower potential improvement in C2MS, for example, if there is less pulmonary reserve. In some embodiments of the invention, patients with a higher Peak VO2 are assumed to have more pulmonary reserve.

In some particular embodiments of the invention, C2MS is applied without using atrial leads, for example, using a device which only has one or two ventricular leads. Optionally, atrial arrhythmia is detected by analyzing signals from one or more ventricular leads only (e.g., to detect activation signals in a time when no activity is expected from the ventricle and/or which falls into an expected atrial activation window, e.g., based on a timing model of the heart, for example, base don an expected range of delays between atrial activation and ventricular activation and/or an expected refractory window of the ventricles). While the accuracy and sensitivity may be reduced, in some embodiments of the invention, all that is needed may be an indication that an AA is in progress. In some embodiments, such analysis may include multiple heartbeats, so while AA may be detected, the detection may take longer than one beat time. In some embodiments, one or all the leads are in the atria (e.g., as explained below) and timing of stimulation from such a stimulation lead uses measured ventricular activation time or estimated ventricular activation time, based on sensing from the atria (e.g., atrial activation plus an expected and/or programmable AV delay).

In some embodiments of the invention, C2MS is applied using a logic which only excludes some or all ventricular arrhythmic beats from such application, but does not exclude all supra-ventricular arrhythmia beats from application of C2MS. A potential advantage is the ability to apply effective C2MS therapy even if most or all beats have an atrial arrhythmia.

An aspect of some embodiments of the invention relates to reducing the prevalence of atrial arrhythmia, for example, reducing the occurrence and/or length of AF episodes, optionally reducing a severity of an existing AF condition and/or preventing such condition from occurring and/or worsening and/or becoming more functionally symptomatic.

In some embodiments of the invention, application of the C2MS signal uses parameters suitable to reach the atria and affect conduction properties therein. AF may be reduced at the source, in at least part of the atria (e.g., left and/or right), optionally the part which conducts to the rest of the heart.

In some embodiments of the invention, application of the C2MS signal to the atria is by a lead in the atria.

In some embodiments of the invention, application of the C2MS signal uses parameters suitable to reach the AV node and/or ventricular tissue which carries activation signals to the rest of a ventricle, for example, one or more of the His bundles, ventricular left and/or right bundles and/or Purkinje fibers. Optionally, this reduces functional symptoms of AF, as extra atrial activations do not get propagated in and/or to the ventricle, for example, by increase a refractory period (relative and/or absolute) in such tissue.

In some embodiments of the invention, as needed, one or more application parameters may be modified, for example, amplitude, delay from local activation and/or electrode location, according to a desired effect (e.g., effect on atria).

In some embodiments of the invention, the application is selected according to a desired effect of reducing a probability of an atrial arrhythmia occurring in a series of next 10 beats, next 50 beats, next 100 beats, next 300 beats, next 1200 beats, next 3600 beats, next 5000 beats or smaller intermediate or larger number of beats, by at least 10%, 30%, 50%, 70%, 80% or intermediate or larger percentages. Different desired effects may be selected (e.g., and/or monitored for), for example, base don patient disease severity, patient stability and/or the amount of extra C2MS application needed while considering side effects of such C2MS application (such as pain) or available battery power. For example, more aggressive reductions may be desirable if pain is of a lessor problem.

In some embodiments of the invention, the estimated prevention probability is estimated based on a table collating information from multiple studies. Optionally or additionally, the information is personalized, for example, the implanted device (or an external processor receiving logs) tracking the duration and/or magnitude of an effect of a C2MS signal on occurrence of AF episodes thereafter. This data may be used, for example for programming a device, for updating said table and/or for setting automatic parameters of the device, for example, parameters which tradeoff power drain due to C2MS application vs effectiveness in reduction of AA. It is noted that an overall healing effect is to be expected in some patients and the overall prevalence and/or duration and/or severity of AA episodes can be expected to go down for such patients, as treatment progresses. Optionally, this is used to update (optionally automatically) the parameter settings of the implanted treatment device, for example, reducing amount and/or duration and/or modifying application location and/or other parameters of C2MS.

An aspect of some embodiments of the invention relates to applying C2MS to the ventricle using an electrode located in the atria. In some embodiments of the invention, the application is between an electrode in the atria and an electrode outside the atria, for example in the ventricle. In some embodiments of the invention, the application uses a bipolar electrode in an atria (e.g., left and/or right). It is noted that a risk of fatal arrhythmia may be reduced by the fact that atrial arrhythmia do not usually fatally propagate to the ventricle (e.g., due to AV node filtering down the frequency and/or the ventricle responding only as fast as its refractory rate), so even if such application causes arrhythmia in the atria, it will not be fatal. It is further noted, that in a patient with AF, there is already atrial arrhythmia, so a C2MS signal applied in a non-refractory time of the atria is not expected to cause further dysfunctional arrhythmia. In some cases, such a signal is not expected to increase heart rate of ventricle.

In some embodiments of the invention, the signal may be applied at a time which is not a refractory (or absolute refractory) period in the atria, while being an absolute refractory period in the ventricle.

In some embodiments of the invention, such an atrial electrode is used for applying other therapy, for example, anti-arrhythmic pacing to the atrium.

An aspect of some embodiments of the invention relates to applying C2MS with parameters suitable to stop an ongoing AF episode. In some embodiments of the invention, the C2MS parameters are set so that they have an effect of cardioversion, for example, by forcing a significant part of the atrium into a refractory state and/or activating such parts. In some embodiments of the invention, the parameters are changed (e.g., amplitude reduced) after such treatment, for example, once the AF episode is assumed to be over and/or restarted if AF is detected again. In some embodiments of the invention, a therapy device tracks which signals seem to have a better effect on AF for that particular patient and/or for different atrial arrhythmia episodes, so that such signals can be automatically applied, when needed.

A potential benefit of using C2MS during an AF episode and/or for an AF patient is increasing cardiac output to compensate, at least in part, for cardiac output reduced due to AF. For example, increasing contractility may enable smaller LV end systolic volume, which may enable better filling from the left atria, potentially overcoming, at least in part, the loss of atrial kick in AF. This potential benefit is optionally realized even if the C2MS does not affect the current or a later atrial arrhythmic episode.

In some embodiments of the invention, the amplitude of a signal applied to treat an ongoing AA episode is allowed to be greater (e.g., by between 10% and 500%, for example, between 10% and 60%, 60% and 150%, 150% and 300%, 300% and 500%, or greater or intermediate percentages) than a chronic application. This may be, for example, due to pain or other side effects being less critical to a patient if the patient is aware of the treatment increase being transient and/or being for treating an acute medical condition.

An aspect of some embodiments of the invention relates to a relationship between a number of stimulations and an improvement in peak VO2, which can optionally lead to an improvement in heart failure symptoms. In some embodiments of the invention, at least for AF patients, increasing the number of treated beats on a monthly basis increases a health benefit to the patient. In some embodiments of the invention, the number of treated beats (per day) is increased to be above 15,000, for example, above 17,000, for example, above 20,000, optionally up to 25,000 optionally up to 35,000 and/or above and/or intermediate numbers.

In accordance with some embodiments, it is noted the effect of treated beat increase may be monotonic, at least over a certain range and/or may otherwise be known, and this may be used to trade off an amount of treatment (and therefore effect) and potential side effects and/or power usage.

An aspect of some embodiments of the invention relates to treating two conditions in the heart using a single non-excitatory signal application for example, treating heart failure and atrial arrhythmia using a single C2MS signal, optionally applied in a single chamber.

In some embodiments of the invention, one condition is heart failure and the other condition is one of atrial arrhythmia, regurgitation and HOCM.

In some embodiments of the invention, the two conditions are treated in different heart chambers, for example, one atria and one ventricle, with the non-excitatory signal being from one of the chambers and reaching to the other.

In some embodiments of the invention, one or more application parameters of the signal application are optimized to provide a better tradeoff between the two diseases being treated. In one example, a time of application, power level and/or a location (e.g., within a chamber and/or which chamber or other location) of application of a C2MS signal may be modified so that even if contractility improvement is reduced, the electrification hits a desired tissue (e.g., atria, AV node, conduction fibers, healthy tissue, diseased tissue, sensitive tissue) at a desired time. In one example, a C2MS signal is applied earlier in order to ensure it hits the atria at a correct timing, for example, for cardio version or AF prevention. In another example, an electrode location, which is sub-optimal for cardiac output is selected, to ensure sufficient coverage of the atria.

In some embodiments of the invention, the other condition being treated may be a structural heart disease and/or an implant. For example, C2MS application location may be optimized so a prosthetic heart valve anchoring is improved and/or may be modified so as to reduce an amount of regurgitation (in a mitral implant, such as a clip or a valve or even when there is no implant). Such valve can be, for example, a mitral, pulmonary, aortic and/or tricuspid valve.

In an example of reducing regurgitation, optionally C2MS is applied in a manner, which reduces heart rate. For example, using C2MS to increase cardiac output instead of increased HR, may allow less regurgitation to occur, if regurgitation is dependent on heart rate. This type of logic may be used for example, if a patient has demand pacing.

For example, C2MS may be selected instead of some or all of a pacing rate increase. In another example, a sensor in the atria or chamber may be used to detect regurgitation and trigger C2MS application. In another example, such a sensor (e.g., a pressure sensor) may be used to detect an increased demand and provide C2MS so that the heart will not need to increase its own heart rate to meet such demand. In another example, a higher heart rate may be associated with increased risk of AA and is therefore to be avoided (e.g., with a suitable threshold or other logic programmed in the device). In another example, heart rate is reduced if AA is detected (e.g., using an electrical activity sensor).

It is noted that here and in other embodiments, while a C2MS signal is described, acute change in contractility need not be provided. Rather, C2MS, unless otherwise indicated, is used to denote non-excitatory signals which cause an immediate and/or ultimate increase in cardiac output and/or change in fetal gene program.

An aspect of some embodiments of the invention relates to shortening a prohibition period after suspected arrhythmia, when applying C2MS. In one example, a suspected ventricular arrhythmic beat causes a prohibition window of only a single or optionally no beats. Potentially, this allows the next C2MS to act on the tissue which is still recovering from an arrhythmic beat. Possibly, this reduces pro-arrhythmic tendencies of an arrhythmic beat and/or otherwise improve functioning and/or potential healing of tissue with heart failure or other dysfunction. In some embodiments of the invention, the length of prohibition window depends on the number of arrhythmic beats (and/or a time duration of a ventricular arrhythmic episode). In some embodiments of the invention, there is no window of prohibition of atrial arrhythmic beats, even if there is a window for ventricular arrhythmic beats. In some embodiments of the invention, C2MS signals are applied even when the atria is excitatory.

In some embodiments of the invention, the prohibition window is shortened and/or C2MS applied during atrial excitatory times even in a heart without atrial arrhythmia and/or when there is no active atrial arrhythmia.

In some embodiments of the invention, a relatively low threshold for heart rate is used, for example, between about 90 or about 100 and about 110 beats BPM. Potentially, this prevents wasting energy on high heart rates (as they have more beats in a same time window and an exemplary treatment is a daily period of 7 hours) and/or may direct more of the applied energy to lower heart rates where the body is at rest.

In other embodiments a higher heart rate threshold may be used, for example, 120, 130, 140- or intermediate heart rates.

It is noted that heart rates may be measured approximately and/or rather than a threshold, some type of fuzzy decision making or hysteresis may be used to decide on prohibition. For example, a signal may be prohibited with a probability that depends on the heart rate. In another example, once heart rate goes down, the threshold may be higher or lower than the threshold for stopping treatment as heart rate increases.

In some embodiments of the invention, there are different prohibit windows for different heart rates. For example, between about 80 and 110 no arrhythmic prohibition window is applied and/or between 100 and 130 there is a one beat length prohibition window and between 120 and 160 there is a two beat prohibition window.

An aspect of some embodiments of the invention relates to detecting atrial arrhythmia from ventricular electrodes. In some embodiments of the invention, AA, for example, AF is detected based on a lack of a P wave, optionally together with an elevated heart rate. In some embodiments of the invention, if the system includes two leads in the ventricle, the two leads are used together as a bipolar ECG sensor. In some embodiments of the invention, the distance between the ventricular leads (if two are used) increases the distance that electrical activity can be sensed using the leads. Optionally, during a calibration phase, various pairing of electrodes on the leads and the casing are tested and pairings which better detect a P wave (or atrial arrhythmia directly), may be selected for use in detecting AF. Optionally or additionally, each lead is used to separately detected lack of P wave. Optionally, a threshold of sensing of P wave is set for each lead. Optionally, a P wave is said to be lacking if one or both (depending on desired reliability and/or sensitivity of the particular lead) of the leads do not detect a P wave. Optionally, a score for AA is calculated based on number of leads that detect P wave, certainty of detection, increased heart rate and/or comparison to a baseline measured of the patient.

An aspect of some embodiments of the invention relates to a planning process for patients. In some embodiments of the invention, a patient with AA or a risk of AA and who may have heart failure, is presented. Such patient is optionally treated using C2MS, for example, by implanting a therapeutic device and/or by reprogramming an already implanted device. Treatment of a patient using electrical stimulation may cause side effects and may also require tradeoff between different results, for example, pain level and reduction in AA. In some embodiments of the invention, an initial treatment is set and the treatment parameters are changed (and implanted device reprogrammed) according to the effect of the treatment. It is noted such reprogramming may be needed even if the initial treatment plan is perfect, for example, due to change in the physiological state of the patient.

In some embodiments of the invention, the caregiver considers a plurality of considerations (e.g., as described herein), including, for example, a level of pain, a desired anti-AA effect, desired heart-failure related effect, potential locations for electrodes and leads, and/or type of existing cardiac arrhythmia (e.g., ventricular) of the patient.

In some embodiments of the invention, a computer or table is used to decide on an initial therapy. For example, the computer may include rules or tables that indicate parameters and their expected effects and a caregiver may select or be offered a treatment plan that meets the various requirements set. Optionally or additionally, a caregiver can input such a proposed treatment plan and have it evaluated by such computer.

In some embodiments of the invention, the computer is programmed using a data set collating one or more therapeutic effects of one or more treatment plans with one or more parameters on patients with one or more characteristics. In some embodiments of the invention, such data set is analyzed using machine learning methods to generate a parametric model (or other model) which can be queried to evaluate an expected range of effects of a treatment on a patient or which can be used to automatically or semi-automatically search for proposed therapies.

In some embodiments, if a patient has an implant capable of providing cardiac contractility modulation treatment in addition to whatever other treatment the implant can provide, a plan to provide cardiac contractility modulation treatment based on the patient's cardiac condition and/or the patient's pulmonary condition is provided.

In some embodiments, the patient's AA condition and/or other condition (e.g., pulmonary condition) is evaluated for suitability for providing cardiac contractility modulation to improve such condition. For example, such improvement may be an increase Peak VO2. In some embodiments, the patient's pulmonary condition is evaluated for existence of pulmonary limitations. If the patient's pulmonary condition is such that the patient can benefit from an improvement in Peak VO2, it is planned to provide cardiac contractility modulation treatment, either with additional cardiac treatment(s), or cardiac contractility modulation treatment on its own. Such additional treatments may include one or more of, for example, pharmaceutical treatment, mechanical implants, electrical stimulation, ablation and/or surgery. It is noted that the parameters of C2MS treatment may depend on such additional treatment, for example, C2MS being used to compensate for or work synergistically with such other treatment.

In some embodiments, the patient's cardiac condition is evaluated to determine whether a cardiac treatment in addition to cardiac contractility modulation should be provided. If the patient's cardiac condition is such that the patient can benefit from an improvement in Peak VO2 or other physiological parameter, then a plan is made to provide cardiac contractility modulation treatment. If the patient's cardiac condition indicates that additional cardiac treatment is desirable, optionally a plan is made to provide cardiac contractility modulation treatment with additional cardiac treatment(s), with optional changes in one or more C2MS parameters accordingly.

In some embodiments, a treatment plan for the patient is selected, which may include providing only cardiac contractility modulation treatment; providing cardiac contractility modulation treatment in combination with treatment for the patient's cardiac condition; or not providing cardiac contractility modulation treatment.

In some embodiments, a potential patient is identified, test are performed to assess and/or quantify one or more of the patient's pulmonary or other physiological condition and cardiac condition, and a cardiac contractility modulation treatment is optionally selected that is suitable, potentially most suitable, for the patient.

Such computer as used for planning may be provided as part of a programmer. In some embodiments of the invention, the computer is a cloud instance or remote server accessed by a local interface.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Cardiac Electrification

Referring now to the drawings, FIG. 1 is a schematic showing of a heart 100, showing various tissues and electrode/lead locations in accordance with some embodiments of the invention.

Referring first to parts of the heart, the following are indicated: a left ventricle 102 with an LV free wall 102, a ventricular septum 106, an aortic valve 108, a mitral valve 110, a left atrium 112, an aorta 114, an atrial septum 116, a pulmonary artery 118, a right atrium 120, an AV node 122 at a bottom of atrial septum 116, a right ventricle 124 with an RV free wall 126, a tricuspid valve 136 and a pulmonary valve 138.

Also shown are a first stimulation lead 130 contacting ventricular septum 106 with an electrode 134 and a second stimulation lead 128, contacting ventricular septum 106 with an electrode 132, at a second location thereon. In some embodiments, a single lead will be used, which includes two spaced apart stimulation electrodes. Optionally or additionally, a lead may include one or more sensing electrode.

While contact electrodes are noted, other types of electrodes may be used as well, for example, screw-in electrodes, sutured electrodes and free-floating electrodes.

In some embodiments of the invention, the stimulation is bipolar, with electrodes 132, 134 each being bipolar electrodes (e.g., a pair), for example in the form of a tip surface and a ring electrode surface and/or acting themselves as a bipolar pair (e.g., one on each lead). Optionally or additionally, a remote electrode (e.g., a device can) acts as a second electrode, e.g., for unipolar stimulation. In some embodiments of the invention, two leads are used, with each lead acting as one pole of a bipolar stimulation.

In some embodiments of the invention, C2MS is applied at both leads (or if more than two leads, optionally at a greater number than at two leads), for example simultaneously and/or interleaved and/or in sequence. The two C2MS signals may be the same or they may be different, for example, in delay, length of a phase, inter-phase delay, amplitude and/or other parameters. This may be useful, for example, if each lead is meant to affect different tissue types and/or have potentially different therapeutic effects. It is noted that in some embodiments, stimulation at a lead is avoided if that stimulation causes unpleasant sensations. In some embodiments of the invention, however, some sensation is allowed, for example, for acute treatment of AA.

In some embodiments of the invention, the C2MS is applied in contact with the ventricular tissue or within ventricular tissue. In some embodiments of the invention, the application is from a distance of, for example, 0-5 mm, 5-10 mm, 10-20 mm, 20-30 mm or intermediate or greater distances form ventricular tissues.

Leads 128 and/or 130 may be dual use, for example, providing a pacing, cardioversion and/or defibrillation signal, in addition to a non-excitatory signal such as a C2MS signal.

In some embodiments of the invention, leads 128 and/or 130 may be used for sensing of electrical activity, optionally using the same electrodes as used for stimulation. In some embodiments, only one lead and/or only one electrode are used for treatment. For example, a single ventricular or atrial lead may be used. Optionally or additionally, a lead outside of the chambers is used in addition to or instead of an intra-chamber lead, for example, in a coronary sinus or other blood vessel, outside the heart (e.g., on/attached to an external surface thereof and/or in a left side of the heart, for example, left ventricle 104 and/or left atrium 112).

It is noted that this figure is schematic and flattened. For example, in a real heart left atria 112 and right atria 120 both abut atrial septum 116.

Exemplary Cardiac Therapy Device

Figure 2:
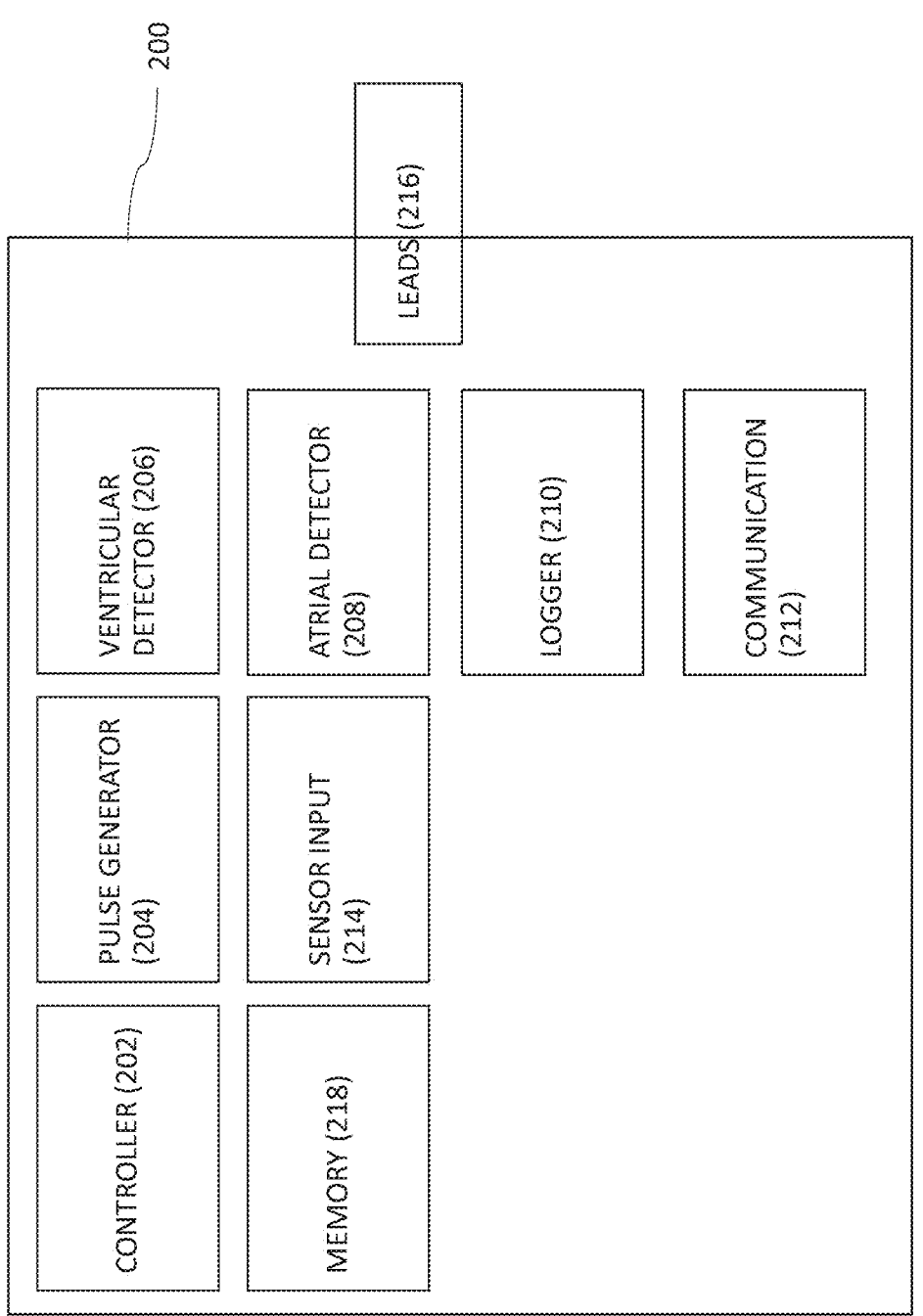
FIG. 2 is a schematic block diagram of a cardiac therapy device, in accordance with some embodiments of the invention.

FIG. 2 is a schematic block diagram of a cardiac therapy device 200, in accordance with some embodiments of the invention. While existing devices such as the Optimizer 4 sold by Impulse Dynamics may be used, other device designs may be used as well and/or may require special settings or reprogramming.

Device 200, as shown, includes one or more leads 216 (optionally two leads), which are optionally couplable to device 200 at one or more can connectors (not shown).

A pulse generator 204 (as an example of stimulation circuitry) is optionally used to generate the signal, for example, including a power circuitry, for example, including one or more storage capacitors.

In some embodiments of the invention, a ventricular detector 206 is provided and used to detect atypical ventricular activation, which can be a contra-indication to signal application.

In some embodiments of the invention, an atrial detector 208 (as an example of an atrial arrhythmia circuitry) is provided and used to detect atypical atrial activation, which may be used as an input to decision making by device 200.

A sensor input 214 may receive data from one or more sensors, for example electrical sensors or other sensors, such as flow, pressure and/or acceleration sensors. Data from the sensors is optionally further processed (e.g., by a controller 202 and/or detectors 206, 208) and are optionally be used as an input to decision making processes in device 200.

A controller 202 (as an example of decision circuitry) is optionally provided and executes one or more logics to decide, for example, a timing and/or other parameters of a signal and/or if a signal is to be applied.

A memory 218 is optionally provided, for example, to store logic, past effects, therapeutic plan, adverse events and/or pulse parameters.

A logger 210 is optionally provided to store activities of device 200 and/or of the patient. Such a log and/or programming may use a communication module 21 (e.g., of a type known n the art) to send data from device 200, for example, to a programmer (not shown) and/or to receive data, for example, programming, for example, pulse parameters.

It should be appreciated that the methods described herein are, in some embodiments, implemented as methods of controlling the operation of device 200, via circuitry (e.g., controller 202, memory 218) thereof and/or methods of programming the device and/or of selecting patients for which the device may be used as therapy and/or planning (and optionally setting up) parameters of therapy for patients. Any such method may functionally terminate at the stage where device 200 is instructed by the circuitry to electrify leads. Device 200 may also be used to test these methods in a test bed with no human subject.

It should be noted that when planning therapy, the planning may include one or more goals, which may be traded-off, for example, considering patient quality of life and device characteristics. Various goals and settings which may be used for approaching the goals and various tradeoffs which may be taken are described in this application (not always in a same embodiment) and one or more of them may be used in an actual planning activity of a single therapy, which may use goals and settings described in the context of different embodiments.

In some embodiments of the invention, planning comprises planning using a planning system (e.g., local client and a cloud server) which shows expected effects of treatment on a patient. Such expected effects may be determined, for example, using rules as described herein and/or using a data set of previous patients (and/or the current patient) and effects of treatment on them. Such data set may be processed using machine learning methods to extract relationships between one or more patient characteristics, one or more stimulation parameters and one or more clinical and/or quality of life effects. Such relationship may be provided for example, in the form of rules, a table, a neural network and/or other software component, optionally provided in tangible form, such as a computer memory.

18

Exemplary Stimulation

Figure 3:
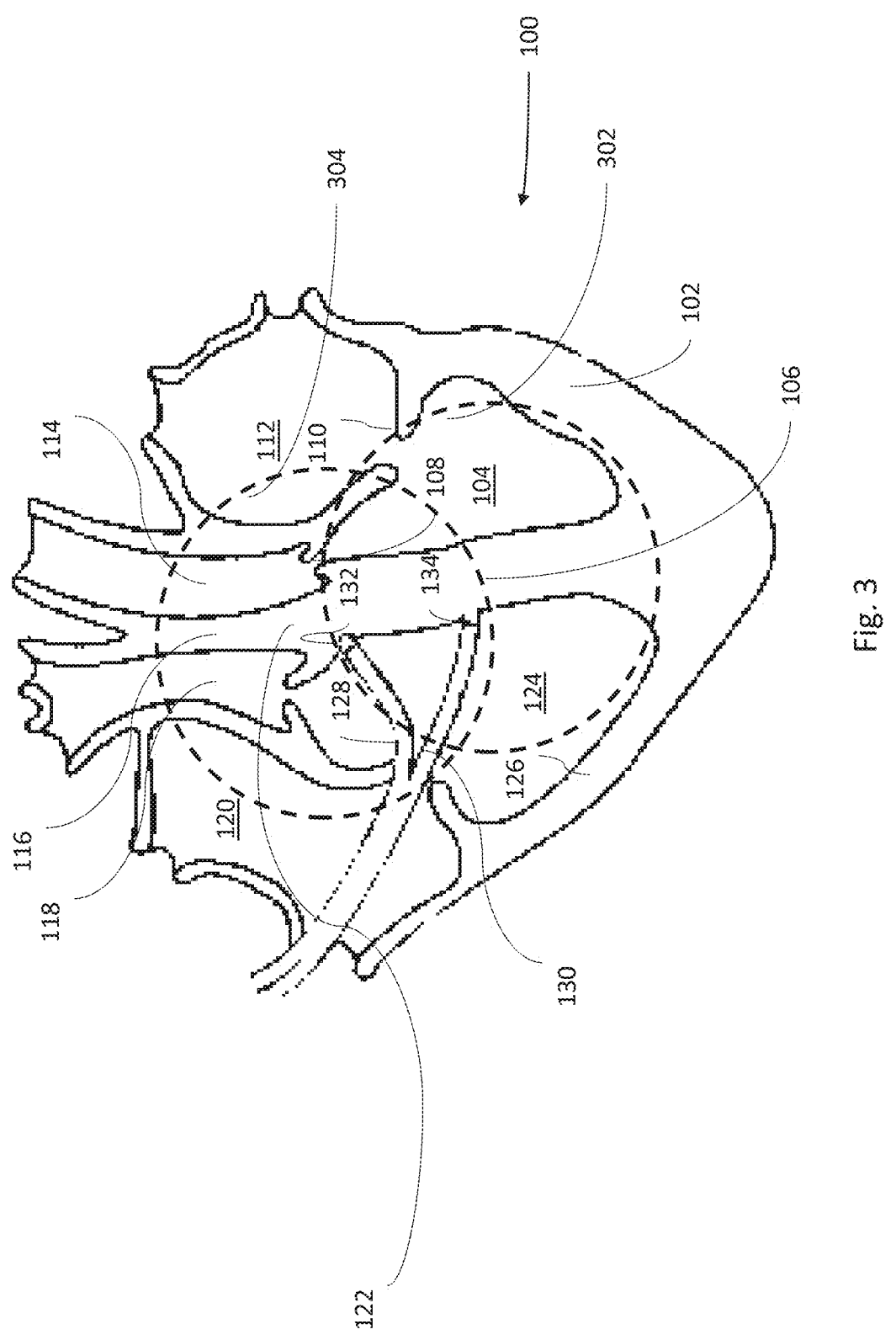
FIG. 3 is a schematic showing of a heart, showing the spatial reach of non-excitatory fields in accordance with some embodiments of the invention.

FIG. 3 is a schematic showing of a heart similar to that of FIG. 1 and also showing the spatial reach of non-excitatory fields in accordance with some embodiments of the invention.

While the heart is 3D and the schematic showing is not spatially correct, a circle 302 is used to schematically show a range within which the amplitude of a signal applied by lead 130 is sufficient (e.g., amplitude) to have a contractility modulating effect (and/or other therapeutic effect such as reversal of gene program and/or other physiological effect such as a functionally meaningful increase in phosphorylation of phospholamban) on cardiac tissue. It is also noted that the figure shows the lead entering from the inferior vena cava. In some embodiments of the invention, the leads enter the right atrium via the superior vena cava (e.g., being inserted through the subclavian vein) or via a different location (e.g., through a heart wall or remain inside cardiac vessels and/or epicardially).

Circle 304 shows a same range for lead 128. The size of the circle is affected, by, for example, the signal amplitude (stronger amplitude reaches further). In addition, the interaction between the signal and the tissue may be affected by other parameters, for example, timing relative to local activation and tissue type.

As can be seen, different leads can reach different tissues at a same signal amplitude. For example, circle 302 includes part of LV free wall 102, while circle 304 can include parts of RA 120, AV node 122 and/or LA 112.

In some embodiments of the invention, the location of the electrifying lead and/or pulse parameters are selected according to desired effects on one or more of these tissues and/or tradeoffs of these effects.

It is noted that if there are actually two leads in the heart, some signals may be applied to one lead and some to the other, so as to provide multiple types of effects and/or tradeoffs.

It is also noted that in FIG. 3 both leads are shown in RV 124 against ventricular septum 106. However, one or more stimulating leads may be in other locations, with consequently different effect circles (e.g., 302, 304) and/or targeting different tissues. In some embodiments of the invention, the leads are located inside the heart, on the right side thereof optionally to take advantage of two potential advantages: a. less out-of-heart tissue being stimulated; and b. less invasive access and/or presence than in the left heart.

Referring to circle 302, it is noted that mainly ventricular tissue is affected. Such effect may include extending a refractory period of tissue conducting electrical impulses from AV node 122, with a potential benefit of preventing atrial arrhythmia from causing ventricular arrhythmia. Optionally, the timing of stimulation is selected so as to extend the refractor period of the relevant conduction tissue.

Such effect may also include a significant conditioning effect (e.g., for fetal gene program remodeling) of both septum 106 and free wall 102 and/or other parts of left ventricle 104.

Referring to circle 304, it is noted that the AV may be stimulated by the C2MS field. Potentially this will reduce its propensity to pass atrial activation on, potentially reducing the symptoms of AF by preventing out of timing ventricular beats.

Potentially, atrial tissue (left and/or right) are stimulated by the signal. Potentially this may damp AA, for example stopping a paroxysmal AF episode.

Exemplary Pulse Parameters

While not being limited to a single pulse sequence, the term C2MS is used to describe any of a family of signals which includes a significant component applied during an absolute refractory period and which has a clinically significant effect on cardiac contractility in an acute and/or chronic fashion and/or which causes a reversal of fetal gene programs and/or which increases phosphorylation of phospholamban. In some embodiments, the signal is potentially excitatory to one part of the heart but non-excitatory to other parts. For example, a signal can be excitatory in atria, but applied at a timing (relative to ventricular activation) when it is not excitatory in the ventricle.

In some embodiments of the invention, the signal while potentially stimulatory during the receptive period of the cardiac cycle, is non-excitatory due to its timing. In particular, the signal is applied during the refractory period of the tissue which is affected by it and, optionally, within the absolute refractory period thereof.

In some embodiments of the invention, the atrial absolute refractory period is assumed to be about 0.15 seconds, followed by a relative refractory period of about 0.03 seconds. In some embodiments of the invention, the ventricular absolute refractory period is assumed to be between 0.25 and 0.3 seconds, with an additional relative period of 0.05 seconds. It is noted that these times can change between hearts and also under different conditions, such as pharmaceutical intake, anatomic excitation level, heart rate, recent arrhythmia and/or exercise and/or may be measured (e.g., by device 200). In some embodiments of the invention, the stimulator is pre-programmed with parameters that take such refractory periods into account. Optionally, different numbers are used (e.g. stored in memory 218) for different conditions (e.g., different heart rates).

This may allow the signal to have a high amplitude without causing dangerous arrhythmia. For example, the amplitude of the signal may be at least 2, 4, 10 times, or intermediate times the cardiac excitation threshold. Optionally, the level at which cardioversion occurs is used as an upper limit, or some fraction of said limit, for example, 0.1, 0.3, 0.5, 0.9 or intermediate fractions.

In some embodiments of the invention, the following family of pulse parameters is optionally used for a C2MS signals for uses as described herein.

In the study below, the following C2MS signal was used: a series of two biphasic pulses, having a duration of 5.14 ms (milliseconds) per pulse phase, a voltage of 4.5V-7.5V and at a delay of between 30-35 ms after local activation at application location (using a bipolar lead) and followed by a charge balancing phase of 40 ms. It is noted that local activation is often shortly after start of ventricular activation. In the balancing pulse, all activated electrodes are shorted together. The voltage is probably reduced until there is a lack of sensation.

This signal can be modified. In some embodiments of the invention, the balancing phase can be omitted or provided with a different length, for example, between 1 and 200 ms, for example, between 10 and 50 ms, for example between 20 and 41 ms, or intermediate lengths.

The top voltage can be increased from 7.5V, for example, to 8V, 9V, 10V, 12V, 20V, 40V, 100V or intermediate or smaller values. It is noted that as an acute effect, sensation may not be considered an issue, though arrhythmia, especially ventricular arrhythmia may need to be avoided.

The delay can be shorter, for example, between 1 ms and 30 ms, between 5 and 20 ms, between 10 and 25 ms or intermediate delays. The delay can be longer, for example, between 35 and 50 ms, 50 and 70 ms, or intermediate or smaller or greater delays. It is noted that longer delays may be acceptable in AA patients as causing an arrhythmia in atria (due to C2MS being applied outside of atrial absolute refractory period), may not be an issue in patients with atrial fibrillation. It is noted that this may allow patients with long Av delays to be usefully treated (e.g., by ignoring atrial effects).

The number of phases may be modified as well, for example, being as few as 1, 2 or 3 or as many as 5, 10, 20, 50 or intermediate or greater numbers. The length of a phase may be modified, for example, being between 1 and 100 ms, for example, 2, 3, 5, 6, 6.6, 10, 15, 25, 50 ms or intermediate in length. Also, not all phases need to be the same length and/or same voltage. In addition, while square pluses are optionally used, other pulse shapes may be provided, for example, sinus, curved, triangular and/or symmetric or asymmetric. In some embodiments, there is an inter-phase delay, for example, 1, 2, 4, 5, 6 10, 20 ms or intermediate or smaller or greater delays.

The energy delivered in a beat may be, for example, 0.01, 0.1, 0.5, 1J, 5J, 10J or intermediate or smaller or greater energy levels.

The duration during which pulses are applied to the heart in a beat can be, for example, 5 ms, 10 ms, 20 ms, 30 ms, 40 ms or intermediate or greater durations.

In some embodiments of the invention, any of the above numbers is varied by, for example, 5%, 10%, 20% or intermediate values.

It is noted that the delay may be a calculated delay (e.g., if patient is paced) or an approximation, for example, if two leads are used as a bipolar electrode, the lowest or an average activation time are optionally used to calculate the delay.

In some embodiments of the invention, the C2MS treatment is applied for, for example, 1, 2, 3, 4, 5, 6, 7, 8, 10, 15, 24 or intermediate numbers of hours a day, for example, for 1, 2, 3, 4, 5, 8, 12, 24 weeks or intermediate or greater number of weeks. During a treatment time, each beat is optionally treated or intended to be treated. In other schemes, the treatment may be set according to a target of number of beats treated per day, for example, as noted herein.

It is noted that a C2MS signal is sometimes not applied at a heartbeat for reasons other than dosing. For example, the heartbeat may be deemed unsafe in the sense that a C2MS signal might cause an arrhythmia if applied during that beat. Optionally or additionally, the heart may be allowed to "recover" from an arrhythmic beat for one or more "prohibition" beats.

In some embodiments of the invention (e.g., in the herein described study), the following algorithm is used to decide if to apply a C2MS signal during a given beat:

A first optional section of the algorithm is avoiding stimulation with C2MS is the heart rate is too high, for example, above a cutoff threshold, for example, 90, 100, 110, 120, 130, 140, 145, 160 or intermediate values. Optionally, this may prevent applying C2MS during VT or incipit VT and/or other arrhythmia, which may be detected as a high heart rate.

A second optional section of the algorithm is avoiding stimulation if a delay between two ventricular leads is above a certain threshold, for example, 30 ms, though other numbers may be used, for example, 10 ms, 20 ms, 40 ms, 50 ms and/or intermediate or greater thresholds. A threshold may also be condition dependent (e.g., heart rate, or other cardiac parameters). This delay may indicate multiple foci and/or irregular propagation direction in the ventricle.

An example specific algorithm comprises:

Sensing ventricle contraction in both ventricle leads determine that heart rate is below 110 BPM If detected contractions delay between the 2 leads is greater than 30 mS, define as improper beat For every detected improper beat do not provide C2MS stimulation during the current and the following ventricle contraction (though in some embodiments, C2MS may be provided on next beat and in others the delay may be more than one beat, such as between 3 and 10 beats, or be a time delay, such as between 5 and 60 seconds or longer).

Following detection of improper beat, continue detection of ventricle contractions in 2 leads. Once 2 proper beats (delay less then 30 mS) are detected, deliver C2MS stimulation in that cardiac contraction, at the preset delay In some embodiments of the invention, irregular beats are detected based on an AV delay and/or based on a morphology of an electrogram signal detected at one or more of the electrodes. Other methods of detecting potentially unsafe beats (e.g., beats where the ventricle may be stimulated outside of its absolute refractory period) may be used as well.

Safety and Efficacy of Exemplary Atrial Stimulation

Figure 4:
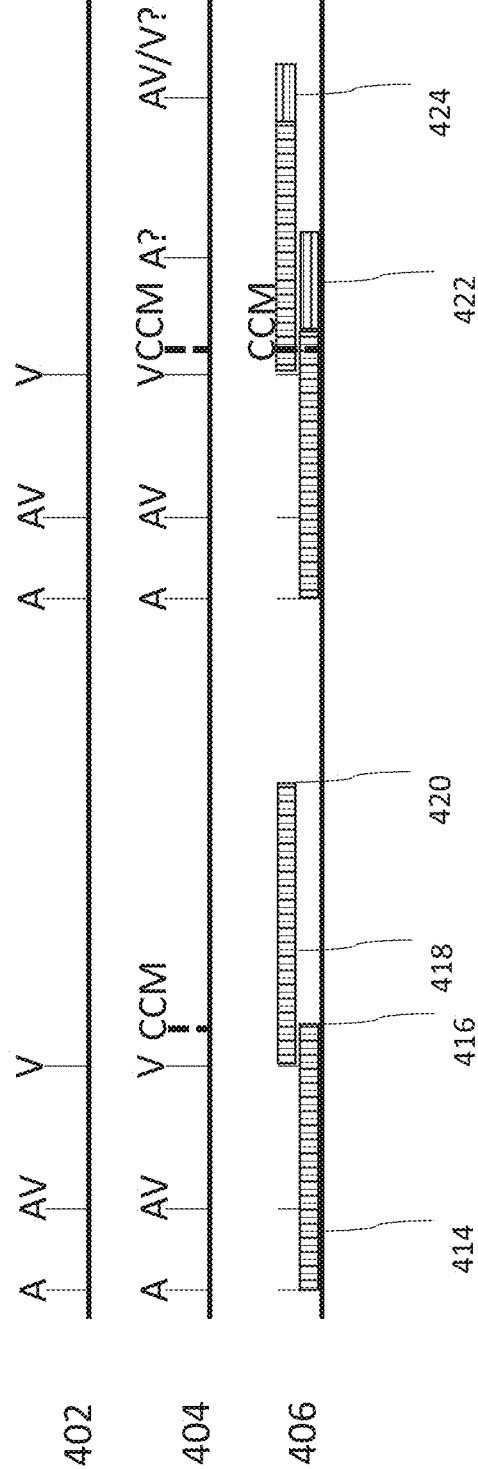
FIG. 4 is a timechart showing the timing of a non-excitatory field in relation to various cardiac events, in accordance with some embodiments of the invention.

FIG. 4 is a timechart schematically showing the timing of a non-excitatory field in relation to various cardiac events, in accordance with some embodiments of the invention.

FIG. 4 includes three time aligned charts (402, 404, 406) showing atrial activation as an "A", AV activation as an "AV" and ventricular activation as a "V". Each time line shows two beats.

Referring first to timechart 402, AV activation happens after atrial activation and before ventricular activation. This reflects activation in the heart starting in the SA node, encompassing the right atria, being conducted by and delayed in the AV node and then reaching the ventricle and propagating therein. The two beats are shown as being identical.

Referring to timechart 404, in the first beat (the timechart being read left to right), a C2MS signal is optionally applied at a short delay after the Ventricular activation, during the absolute refractory period of the ventricle. This can be seen by referring to timechart 406, in which the absolute refractory period in the atria is indicated by 414 (and its end by 416) and the absolute refractory period in the ventricle is indicated by 418, and its end by 420. These refractory periods are shown as if the C2MS signal itself does not affect their duration. As can be seen in the timechart, it can be desirable that the C2MS be applied at a time when also the atria is in an absolute refractory period. In other embodiments, for example, as noted herein, a C2MS signal is applied when the atria is not refractory.

The second beat in chart 404 includes an atrial arrhythmia. A first possibility is marked as "A?", which is when the atria is predisposed to create an arrhythmic activation. In accordance with some embodiments of the invention, the application of the C2MS signal reaches to the atria and extends the refractory period in the atria, as indicated by 422. This can prevent such an arrhythmic activation from occurring and/or prevent it from propagating to the AV node (e.g., if it is the refractory period of AV node tissue which is extended).

A second possibility is marked as "AV/V?" in which an abnormal activation exits the AV node. However, in accordance with some embodiments of the invention, the refractory period of conduction tissue near the AV node is extended, 424, by the C2MS signal and such activation fails to propagate. In accordance with some embodiments of the invention, the refractory period of tissue of the ventricle itself is extended, so even if the activation starts propagating, it is stopped by meeting ventricular refractory tissue.

These timecharts show several possibilities by which a C2MS signal can acutely prevent a ventricular activation from showing significant dysfunction due to atrial arrhythmia. In addition, it is believed that a C2MS signal can entrain tissue to resist arrhythmic behavior.

Timechart 406 shows the possibility that extension 424 of the ventricular refractory period is less than extension 422 of the atrial refractory period. This can be due, for example to the relative timing of the C2MS signal and the tissue activation. When applied closer to the end of the refractory period, it is believed that the extension of the refractory period is increased. U.S. Pat. No. 7,991,469, for example shows how a non-excitatory signal applied during a refractory period can extend the refractory period. In some embodiments of the invention, the application of the C2MS is selected to target the AV node and/or fast conductive pathways such as the Purkinje fibers.

In some embodiments of the invention, the timing of the C2MS is changed, for example delayed more or less, depending on the desired effects, in particular desired effects as they relate to ameliorating AA. Optionally or additionally, C2MS signal application location is changed and/or signal amplitude is changed to select which tissue is to be affected by the C2MS signal. It is noted that the cardiac tissue moves during the cardiac cycle, so such C2MS signal parameter changes optionally take into account the physical distance as it depends on the cardiac cycle. For example, applying C2MS later in systole (from the ventricular septum) can affect more of the free wall of the left ventricle for a longer period, than a similar signal applied before the ventricle contracts significantly. In some embodiments of the invention, the duration of the signal is changed (or the C2MS signal split into two or more time-separated components) so that different parts of the ventricle are stimulated at different times. This may allow the total power delivered to be lowered (e.g., if the goal is reaching a threshold application level at treated tissue). Such modification may be especially important if a C2MS signal is selected to be sub-optimal for C2MS application due to other desired effects.

A tradeoff may be made between the various desired effects. For example, as noted above, an electrode position suitable for the right atrium, might cover less of the ventricle. This may reduce the ventricular effect, but from a clinical perspective, the overall condition of the patient may improve. In a similar manner, if there are two stimulation parameter sets, one of which covers more ventricular tissue but which also causes more mitral regurgitation, a different parameter set which has reduced regurgitation, even if it has reduced or slower-acting therapeutic effect, maybe desired overall. In one example, various stimulation regimens are tested on a patient and the regimen with the desired effect (e.g., on regurgitation of atrial and/or mitral valves or HOCM-type blockage of atrial outflow) is selected. In some embodiments of the invention, the regimen is determined by modeling the heart and its response to stimulation and/or by matching one or more heart parameters to known patients and their response to C2MS. Modeling may be suitable before device 200 is implanted, in order to decide if to implant device 200 and/or when deciding which parameters to change in an implanted device.

In some embodiments of the invention, if two or more leads are used and some effects are chronic, selective activation of such leads may be practiced. For example, if AF is expected or detected (e.g., using the atrial detector), a more atrial lead is used and otherwise (e.g., and/or to meet some desired therapeutic dose) a more ventricular lead is used.

For example, in a case of paroxysmal AF, upon detection of onset of AF, device 200 may deliver C2MS treatment. The stimulation lead can be, for example, in the RV and/or LV and deliver during a refractory period thereof and/or the delivery may be form an atrium and deliver optionally at any time, if the stimulation does not reach the ventricles.

In another example during an ongoing AF episode, optionally of a chronic AF sufferer, device 200 may be used to prolong the ventricle refractory period (by C2MS signal delivery to a ventricle) and/or be used deliver a C2MS signal in the atria that may suppress AF triggering. Referring back to extended refractory periods 422, 424, it is noted that in accordance with some embodiments of the invention, even if a C2MS signal itself causes atrial arrhythmia direction, for example, by directly causing an abnormal activation, this may not be an overall problem if such activation is prevented from reaching the ventricle. The overall therapeutic balance may allow such degradation of atrial function, due to an overall increase in cardiac output and/or health.

Exemplary Stimulation Variations

FIG. 3 has described using a methodology where there are only ventricular leads and atrial sensing is not provided. This has the potential advantage of ignoring AA while still maintaining safety of ventricular application because the ventricle is in a refractory state when the C2MS signal is applied.

In some embodiments of the invention, a setup with atrial sensing is used, for example, by adding an atrial lead (e.g., with one or two ventricular leads). In some embodiments of the invention, such a setup is used to detect AA and potentially treat it and/or its symptoms, for example using a C2MS signal, for example, as described herein or using other electrical treatments, such as atrial anti-arrhythmic pacing. Alternatively, if AA is detected, an additional check is made to see if there are ventricular irregularities. As noted herein, some such ventricular irregularities can be prevented and/or blocked by a C2MS signal. In some embodiments of the invention, such arrhythmia is detected by measuring a delay between atrial and ventricular activation and detecting, for example, if their ratio is 1:1 and/or their relative delay.

In some embodiments of the invention, one or more of the following methods are used to detect arrhythmia (in a current beat or ongoing):

1. Based on heart rate. If the heart rate is over a set threshold, it is considered tachycardia. Below a lower threshold the cardiac state may be considered brady-cardia.
2. If the source of triggering is not coming from the AN node, this can be detected by change in the time interval between the two ventricular septum leads and/or the shape of the QRS detected by the ventricle leads.
3. Heart rate variation (HRV). If HRV is high (e.g., above a threshold) this may indicate a ventricular arrhythmia.

In some embodiments of the invention, a safety/irregu-larity detection method such as described in one or more of the following U.S. Pat. Nos. 6,233,487, 6,597,952, 6,263,242, 6,370,430, 6,993,385, 7,953,481, 6,480,737, is used. Other methods may be used as well.

Exemplary Evaluation

In some embodiments of the invention, sensors input 214 and/or controller 202 are used to close a treatment loop.

In one example, sensors can provide an indication of cardiac output or patient activity. Such indication can be used to automatically identify that a therapeutic protocol is working and should be continued.

In another example, acute changes in arrhythmia, heart rate and/or cardiac output (or a proxy) are used to identify if application parameters are acceptable or not.

In another example, sensors are used to detect a need for increased cardiac output. In such case, stimulation param-eters which increase cardiac output, at expense of providing therapeutic goals, such as longer-term suppression of AF, are provided.

In another example, changes in heart rate possibly indi-cate a need to change C2MS signal parameters. For example, changes in heart rate may change the relative timing of activation in two chambers and/or timing of the refractory periods of atria and ventricle. In some embodi-ments of the invention, the timing of C2MS signal applica-tion is changed (e.g., to fall in atrial refractory period or not) to maintain desired arrhythmic-alleviating effects.

Concurrent Drug Delivery

In some embodiments of the invention, C2MS signals are used to provide some anti-arrhythmic effect by extending refractory period and/or by other means. As a result the dosage of such anti-arrhythmic drugs may be modified. For example, the dosage of one or more of the following drug families may be modified (e.g., reduced, and/or allowed to be increased): anti-arrhythmics such as Amiodarone, Fle-cainide, Procainamide and/or Sotalol; Beta-blockers; Cal-cium channel blockers; and/or Ace inhibitors.

In some embodiments of the invention, C2MS application is timed according to drug taking times, for example, to provide more C2MS anti-arrhythmic effect during a time at which the blood levels (or other effectivity indicator of the dug) is lower.

In some embodiments of the invention, C2MS timing is selected according to an expected effect of cardiac drugs on refractory period, for example, to ensure that stimulation is during a refractory period. It is noted that a there are some indications that a signal applied near the end of a refractory period may have the effect of preventing a next activation, which may have an anti-arrhythmic. Timing such activation may depended, for example, on drug dosage and/or expected effect. Optionally, such effects are programmed in memory 218.

Possible Mechanisms of C2MS

Without being necessarily limited to any particular expla-nation, one or more of the following physiological expla-nations may serve to provide some intuition as to how various parameters of treatment may be modified for use for some embodiments of the invention.

As discussed for example in Heart Fail Rev. 2016; 21(6): 645-660, "Cardiac contractility modulation: a novel approach for the treatment of heart failure", the C2MS signal may have contractility improving effects by a direct effect on phosphorylation of phospholamban and/or other direct effect on cell functioning (e.g., other proteins). This may cause a cascade that reverses the fetal gene program and causes functional remodeling of the cardiac tissue affected. In some embodiments of the invention, the amount of phosphory-lation (or other cellular effect as described therein) and/or amount of program reversal is used as a guide for describing what amount of C2MS signal is desired.

With regard to the atria, it is possible that the C2MS signal entrains the atrial tissue, for example, by synchronizing the tissue and preventing variation in activity, which variation may also cause longer-term remodeling of electrical behavior of such tissue.

At an acute level, U.S. Pat. No. 4,554,922, for example, has apparently suggested that electrical signals applied in the relative refractory period extend the refractory period and make tissue less pro-arrhythmic. Such extension may block propagation without generally affected muscle activity. In some cases, the effect is blocking of electrical activity for longer than the inter-activation duration, which does reduce muscle functionality.

VO2 Improvement

Figure 5:
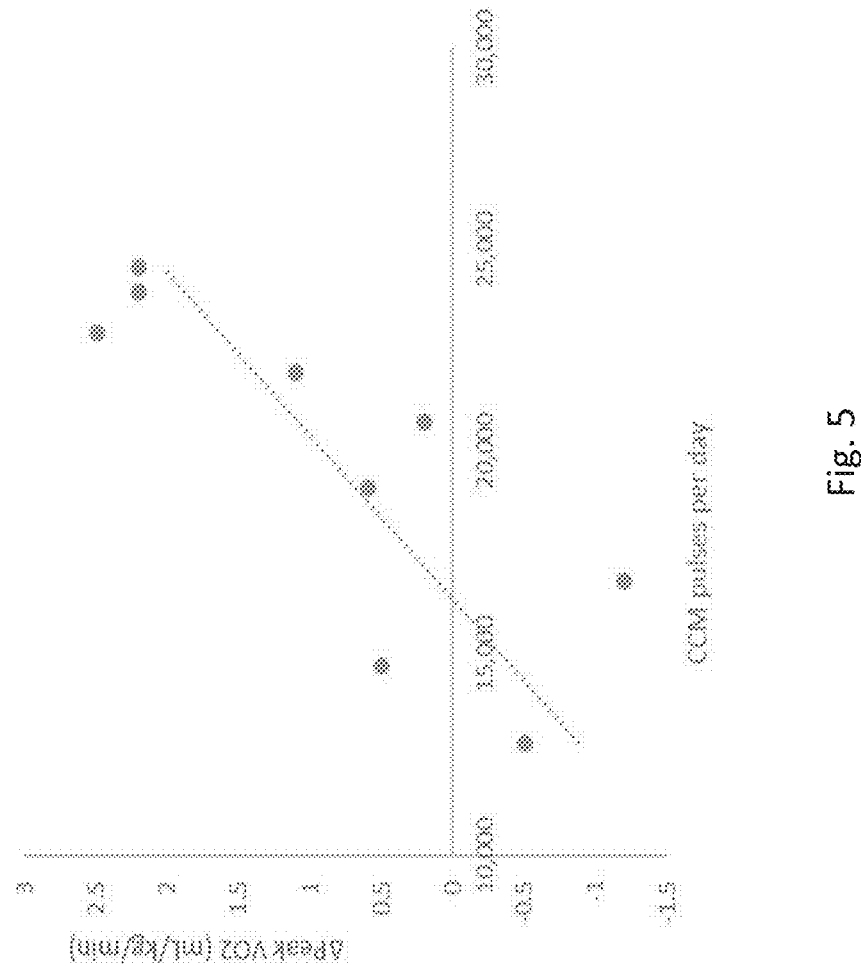
FIG. 5 is a graph showing results of a study in which C2MS improved a VO2 parameter of AF patients, in accordance with some embodiments of the invention.

FIG. 5 is a graph showing results of a study in which C2MS improved a VO2 parameter of AF patients, in accordance with some embodiments of the invention.

In a study, 60 patients were selected and implanted with 2-lead Optimizer Smart System a C2MS device by Impulse dynamics. Of these 9 were patients with atrial fibrillation and the effect of treatment on them is described herein. Patients were selected (and may be selected for treatment after implant. The inclusion and exclusion criteria are summarized in Table 1. Major criteria included: adult subjects with LV EF≥25% and ≤45% by echocardiography (assessed by core laboratory); NYHA III or ambulatory IV symptoms despite 90 days of guideline-directed heart failure medical therapy (including ICD when indicated) that was stable for 30 days prior to enrollment; and, not indicated for cardiac resynchronization therapy (CRT). Patients were excluded if they were hospitalized for heart failure requiring intravenous loop diuretics, inotropes or hemofiltration within 30 days; if they were receiving any form of positive inotropic support within 30 days before enrollment; if peak VO2 on cardiopulmonary stress testing (CPX) was <9 or >20 ml O2/min/kg (assessed by core laboratory); if they had a potentially correctible cause of heart failure (e.g., valvular or congenital heart disease); if exercise tolerance was limited by a condition other than heart failure; or if they were schedule for or had recent CABG, PCI or MI. Notably, in comparison to all prior studies in the United states, patients with atrial fibrillation could be enrolled.

TABLE 1

Inclusion and exclusion criteria.

Incusion Criteria:
1. 18 years of age or older
2. Male or a nonpregnant female
3. Baseline ejection fraction ≥25% and ≤45% by echocardiography core laboratory.
4. NYHA III or IV despite guideline-directed medical therapy for heart failure for at least 90 days (including treatment with a β-blocker for at least 90 days unless intolerant)
    a.    medical therapy is stable defined as no more than a 100% increase or 50% decrease in dose during the 30 days prior to enrollment
    b.    ICD if indicated
5. Willing and able to return for all follow-up visits.
    Exclusion Criteria:
1.    Peak VO$_2$ <9 or >20 ml O$_2$/min/kg. The qualifying CPX test must be deemed adequate.
2.    Subjects who have a potentially correctible cause of heart failure (e.g., valvular or congenital heart disease)
3.    Clinically significant angina pectoris, an episode of unstable angina within 30 days, or angina and/or ECG changes during exercise testing performed during baseline evaluation.
4.    Hospitalized for heart failure requiring acute treatment with intravenous loop diuretics, IV inotropes or hemofiltration within 30 days, or receiving any form of positive inotropic support within 30 days before enrollment, including continuous IV inotrope therapy.
5.    PR interval greater than 375 ms.
6.    Exercise tolerance is limited by a condition other than heart failure or unable to perform baseline stress testing.
7.    Scheduled for CABG or PCI, or has undergone a CABG within 90 days or PCI within 30 days.
8.    Biventricular pacing system, an accepted indication for such a device, or a QRS width of 130 ms or greater.
9.    Myocardial infarction within 90 days.
10.    Mechanical tricuspid valve
11.    Prior heart transplant.
12.    Chronic hemodialysis.
13.    Participating in another experimental protocol.
14.    Unable to provide informed consent.

and/or treatment for such patients planned in accordance with some embodiments of the invention under one or more or all of the criteria described herein below, inclusion and/or exclusion):

Methods: Patients could participate if they had NYHA III/IVa symptoms despite appropriate medical therapy, LVEF 25-45% and were not eligible for CRT. All subjects received an Optimizer 2-lead implant and were seen at 12- and 24-weeks. Device interrogation provided a number of C2MS signals effectively delivered.

Sixty subjects were enrolled from 7 medical centers in the United States and 1 medical center in Germany. Subjects were evaluated at baseline and again at 12- and 24-weeks The schedule of events is summarized in Table 2. Following eligibility determination, subjects underwent implantation of a 2-lead Optimizer Smart System. After device programming, subjects were generally discharged from the hospital the same day or the day following implantation. Subjects returned for routine wound and device checks (when C2MS signal parameters were checked and optimized) after ~2 weeks. Study follow up visits for clinical assessments were conducted at 12- and 24-weeks (±2 weeks) following device implantation. In addition to an interim safety assessment, NYHA was determined by a site clinician and CPX tests were repeated at these visits.

TABLE 2

| | Screening/ Baseline | Optimizer Implant | Week 2 ± 7 days | 12 ± 2 Weeks | 24 ± 2 Weeks | 1 Year ± 1 mo | Every 6 months** |
|---|---|---|---|---|---|---|---|
| Tests and Assessments | | | | | | | |
| Informed Consent | X | | | | | | |
| Interim History | X | | X | X | X | X | X |
| NYHA Class (site clinician assessment) | X | | | X | X | | |
| Medications | X | | | X | X | | |
| Physical Examination | X | | | X | X | | |
| 12-Lead EKG* | X | | | | | | |
| NT-proBNP | X | | | X | X | | |
| Echocardiogram* | X | | | | | | |
| Cardiopulmonary Stress Test | X | | | X | X | | |
| Pregnancy Test | X | | | | | | |
| Eligibility determination | X | | | | | | |
| OPTIMIZER Smart System Implant | | X | | | | | |
| Chest X-ray (prior to hospital discharge) | | X | | | | | |
| OPTIMIZER Device Interrogation | | X | X | X | X | X | X |
| Safety Reporting | | X | X | X | X | X | X |

*12-Lead EKG and Echocardiogram test results (from the study-qualified lab) obtained within 30 days before informed consent and performed in accordance with the protocol, testing, and data collection requirements may be used for eligibility determination and baseline testing
**Visits shall continue every 6 months until the PMA order has been issued by the FDA, for device interrogation and reporting of OPTIMIZER Device related SAEs, if any The general results (also non-AF), include: 60 subjects, 88% male, age 66±9 years, with LVEF 34±6%, 68% having ischemic cardiomyopathy, and 15% with atrial fibrillation were included. C2MS delivery did not differ between 2- and 3-lead systems (19,892±3472 vs 19,583±4998 pulses/day). A change of peak VO2 from baseline to 24 weeks was 1.72 (95% Bayesian credible interval [BCI]:1.02, 2.42) ml/kg/min greater in the 2-lead device group versus the control group. Adverse events did not differ between groups except for a decrease in Optimizer-related adverse events (0% vs 8%, p=0.03) in the 2-lead group compared to the 3-lead group.

Also, NYHA improved by at least 1 functional class in 83.1% of subjects treated with the 2-lead Optimizer system at 24 weeks compared to only 42.7% in the FIX-HF-5C control group (p<0.001).

More details on the study may be found in the co-filed application with 62/924,782.

In general, the patients were selected for the study if there had class III NYHA (though also class IVa were allowed and/or may be used in some embodiments of the invention as may class II) systolic heart failure with ejection fraction between 25% and 45%. In some embodiments of the invention, patients may be selected with an EF between 25% and 55%, for example, between 33% and 45%. In addition, the patients had a peak VO2 of between 9 and 25 mL/kg/min. In some embodiments of the invention, patients are selected if they have a peak VO2 of between, for example, 9 and 12, 12 and 15, 15 and 20, 20 and 25 mL/kg/min or intermediate values. In some embodiments of the invention, it is assumed that a patient with higher peak VO2 has a greater potential of making use of any cardiac improvement provided by the treatment.

As can be seen in FIG. 5, C2MS, when applied to patients with heart failure and atrial fibrillation increased peak VO2 for most patients, with an average over all 9 patients of 0.844 mL/kg/min with a slope level of 0.0025 (e.g., after several months, such as after 12 or 24 weeks) and relative to a baseline; improvement relative to a control is also expected, as control patients typically deteriorate). It is noted that if only patients with a high number of beats treated are selected, the improvement increases. The non-AF patients show an improvement of Average: 1.09, STD: 1.48 mL/kg/min, with apparently no positive effect of number of beats treated. In comparison, when using a three lead device there is a substantial lack of increase in peak VO2 (but also no decrease, which decrease would be expected for such patients) for non-AF patients. This suggests a synergy between patients having AF and patients benefiting from treatment. As noted, this synergy is possibly above and beyond the basic potential advantage of treating AF patients using C2MS signals in spite of AF being a contra-indication.

In some embodiments of the invention, patients with AF are selected for treatment, with a goal of at least 0.5 ml O2/min/kg, at least 1 ml O2/min/kg, at least 2 ml O2/min/kg, at least 3 ml O2/min/kg or at least 7 ml O2/min/kg or intermediate values of improvement in VO2.

In some embodiments of the invention, patients are selected for treatment based on an indication that peak VO2 is limited by cardiac considerations.

It is noted that increase in VO2 may require the patient to have some pulmonary reserve. Optionally, patients are selected if their breathing reserve (e.g., potential increase in pulmonary effectiveness) is at least 10%, at least 20% at least 30%, at least 50% and/or intermediate or greater values. BR below 30 or 33 is often considered low and indicative of a pulmonary disorder which may be limiting on peak VO2 improvement. BR may be defined as the difference between the maximal voluntary ventilation (MVV) and the maximum ventilation measured during exercise test (e.g., BR %=(MVV−VE/MVV)×100).

In some embodiments of the invention, patients are considered to potentially have a useful pulmonary reserve based on their oxygen uptake efficiency slope (OUES), for example, it being below 95%, 90%, 89%, 85%, 70% or intermediate values.

In some embodiments of the invention, patients are considered to potentially have a useful pulmonary reserve based on their peak RER, for example, being above, for example, 1, 1.05, 1.1, 1.15 or intermediate values.

In some embodiments of the invention, patients are considered to potentially have a useful pulmonary reserve based on their AT being low, rather than normal or crossed.

In some embodiments of the invention, patients are considered to potentially have a useful pulmonary reserve based on their VE/VCO2 ratio being above, for example, 25, 30, 35 or intermediate values.

In some embodiments of the invention, patients are considered to potentially have a useful pulmonary reserve based on their O2 saturation not falling and/or not falling rapidly during exercise, for example, falling less than 20%, 10%, 5% or intermediate values over a period of 20 minutes of exercise.

In the alternative (or additionally), it is noted that an improvement in cardiac function may reflect in manners other than VO2 improvement, for example, in reversal of fetal gene program, for example, as evidenced by normalizing of one, two, three or more mRNA, protein level indicators and/or blood peptides. In some embodiments of the invention, patients are selected if they have AF (or other AA, for example, one or more of Atrial tachycardia, Atrial flutter, Sinus tachycardia, Supraventricular tachycardia (SVT), Wolff-Parkinson-White (WPW) syndrome) and heart failure (e.g., reduced cardiac output) even or especially if they do not appear to have a useful pulmonary reserve.

As can be also seen in FIG. 5, the extent of improvement seems to increase as a function of the number of actual treated beats. In particular, above about 17000 beats, there is an average improvement and this improvement increases as the number of treated beats increase to 20,000 and 25,000 beats.

In some embodiments of the invention, this suggests selecting AF patients based on a predicted possibility of treating more beats. For example, surface ECG of such patients may be taken and processed against a simulation of the C2MS application algorithm and selecting for treatment patients where a sufficient number of beats may have C2MS applied therewith.

It is noted that in some patients the C2MS is not applied based on a beat. For example, in patients with AF where C2MS is applied to an atria, there may be no meaningful beat definition and/or application may not be synchronized to an actual beat. In other patients, application is synchronized to an actual or desired beat. Optionally a paced beat is treated. In some cases, the synchronization is what is happening in one chamber (e.g., a ventricle) while ignoring the timing in another chamber (e.g., an atria), in some cases where the stimulation reaches the other chamber and in some cases where it does not. In some embodiments, timing is selected so that application is at a time where both atria and chamber are in a refractory period, even if the beat rates are not synchronized.

In some embodiments of the invention, the duration of treatment (e.g., to be more than 7 hours, for example, based on an estimated number of beats per hour or by number, for example, 8 hours or 9 hours of treatment being allowed) is selected so as to increase the number of treated beats.

In some embodiments of the invention, one or more blocking parameters are relaxed, for example, heart rate, so that beats can be treated at a higher heart rate. For example, heart rate between 110 and 150 or 110 and 130 is allowed to be treated.

In some embodiments of the invention, the device parameters are modified responsive to an actual measurement of applied beats (e.g., as detected during implantation or after, for example, for a period of a day, a week, a month 3 months or intermediate periods.

In some embodiments of the invention, pacemaker settings are modified (e.g., base heart rate increased) so as to allow for more treated beats per day.

In some embodiments of the invention, parameters are adjusted to increase the number of beats per day responsive to the treatment-lacking efficacy, rather than responsive to the number of applied beats. For example, being increased to 30,000, 40,000, 50,000 or intermediate or greater number of beats per day. In some embodiments of the invention, the parameters are modified so that such a number may be reached and once a desired number is reached, stimulation for that day stopped.

In some embodiments of the invention, such selection of a dosage of beats per day is specifically applied for AF patients. In other embodiments, it is applied to non-AF patients.

In some embodiments of the invention, the number of beats is increased responsive to a detection that C2MS application is reducing the number of atrial arrhythmic beats. In some cases, such a determination may indicate the C2MS is not having a sufficient anti-arrhythmic effect and C2MS application is reduced and/or changed, for example, so it is applied mainly for other effects, for example, increase of cardiac output.

In another example, if an atrial (or other) sensor detects increased electrical activity in an atria, an AA is assumed and C2MS delivery which affects the atria and/or the AV node and/or ventricular conduction form the AV node, is increased and/or timing and/or other parameters changed to better deal with AA.

In another example, during an AA episode, if the heart rate of the ventricle increases and actual demand is not (e.g., based on an accelerometer or other activity sensor), increased and/or modified C2MS is applied to the atria.

Exemplary Stimulation from Atria

Figure 6:
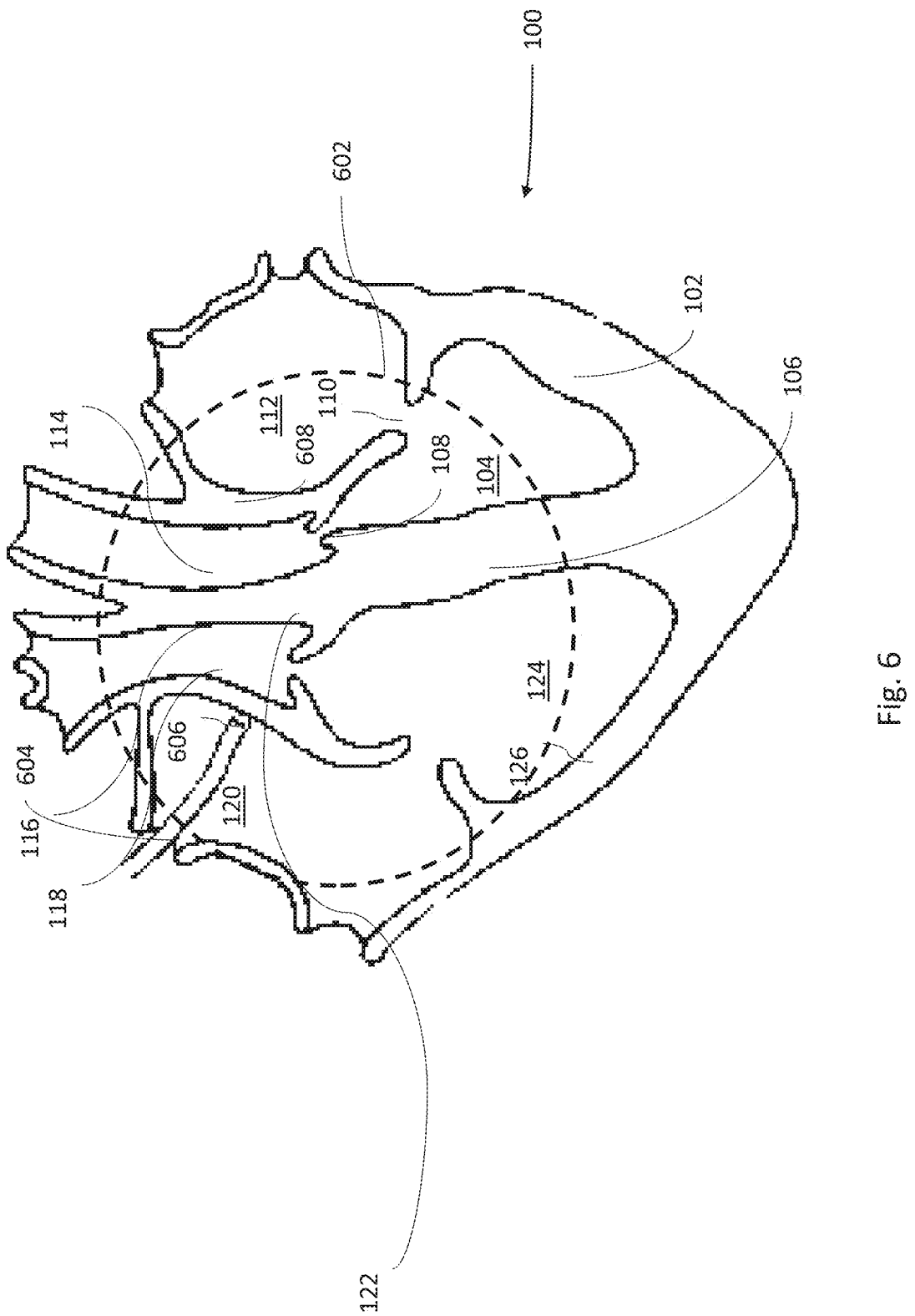
FIG. 6 is a schematic showing of a heart, showing the spatial reach of non-excitatory fields from the right atria in accordance with some embodiments of the invention.

FIG. 6 is a schematic showing of heart 100, showing a spatial reach 602 of non-excitatory fields from the right atria in accordance with some embodiments of the invention.

It is noted that the drawing is distorted, but as can be appreciated, the stimulation signal parameters may be set so that a significant part of the ventricular septum is affected by the C2MS signal, as well as significant parts of the right atrium, left atrium and AV node. It is noted that such effect may reduce AA in one or both atria. Optionally, the pulse parameters are selected so that the C2MS signal reaches the pulmonary veins' junction with the left atria, which may reduce some types of atrial arrhythmia.

As a potential benefit it is noted that applying a C2MS signal in a manner unsynchronized with atrial self-pacing and/or at a timing which causes an arrhythmic episode, may not be as dangerous, as such extra atrial beats may not affect the ventricle (e.g., for reasons noted herein) or at most act as "natural" atrial arrhythmia, which is not, by itself, immediately life threatening. In some embodiments of the invention, an electrode 606 of lead 604 is used to detect signals indicative of ventricular timing, so as to time the stimulation in the atria to be at a short delay (e.g., 1-70 ms) after ventricular activation.

Figure 7:
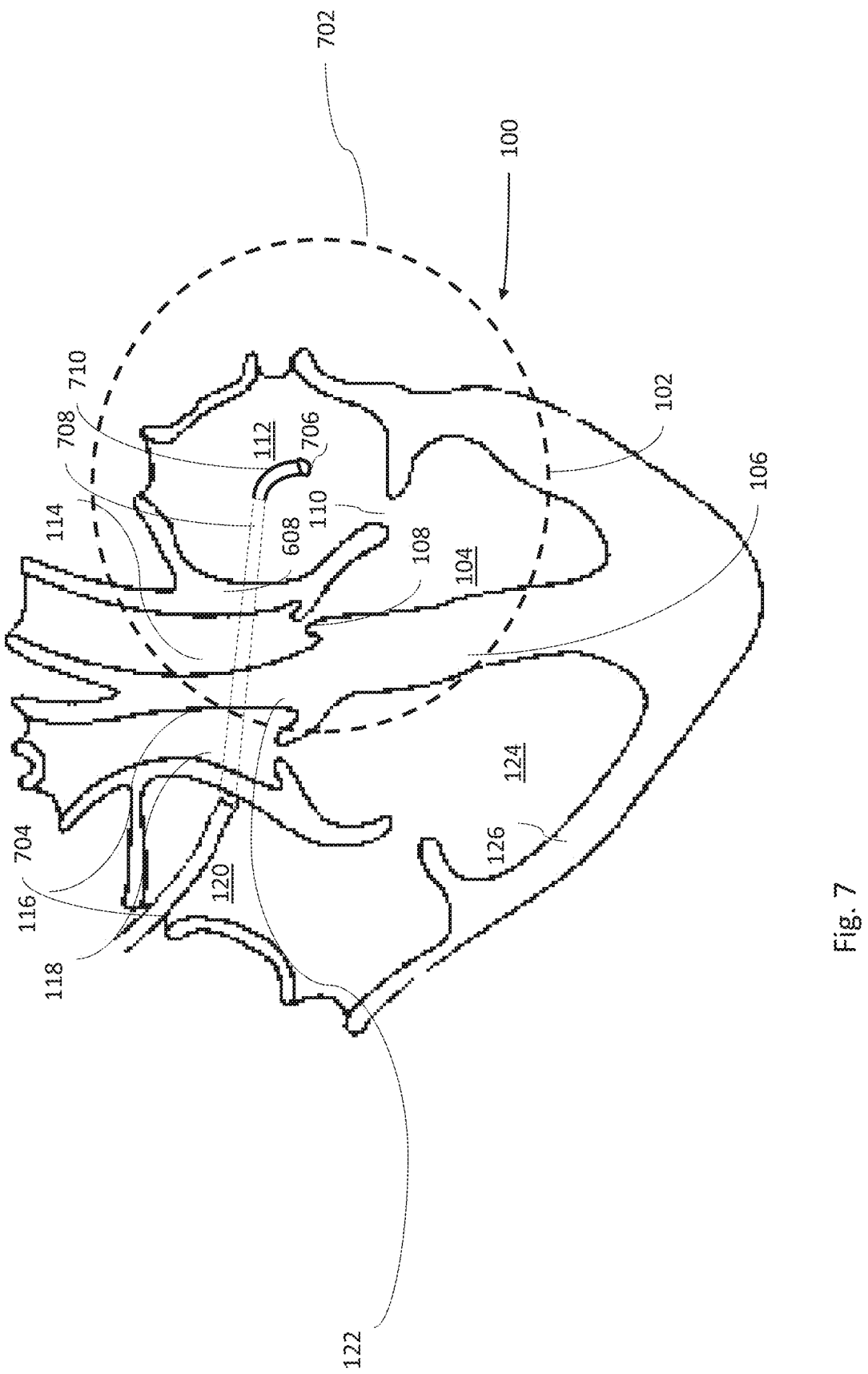
FIG. 7 is a schematic showing of a heart, showing the spatial reach of non-excitatory fields from the left atria in accordance with some embodiments of the invention.

FIG. 7 is a schematic showing of a heart, showing the spatial reach 702 of non-excitatory fields from an electrode 707 of a lead 704 in the left atria in accordance with some embodiments of the invention.

In the example shown, lead 704 is provided in a transseptal approach, dotted lines 708 indicating hidden parts of the lead and noting the drawing is distorted. In the example, shown, lead 704 passes through the atrial septum (e.g., foramen ovalis) and has a curved (optionally pre-shaped) section 710 (e.g., to assist in anchoring and/or in tip placement). Optionally, as shown, tip 706 is placed downwards to be closer to the ventricle. In some embodiments, placement of tip 706 is selected so as to "reach" 702 the pulmonary vein entrances with the C2MS field. In some embodiments of the invention, the electrode location and/or signal strength and/or timing are selected to minimize or avoid a potential effect in the ventricle, other than that of contractility enhancement, if any. A potential benefit of placing an electrode in an atria is that such an electrode can be used to apply a defibrillation-strength signal, albeit, in an amplitude limiting its reach to the relevant atria. Optionally, the timing of such a signal is selected so as to fall during an absolute refractory period of the relevant ventricle (e.g., a ventricle which may be stimulated directly by such field).

It is noted that when stimulating from the atria, it may be necessary to use a stronger amplitude and/or different timing so as to ensure reach of the applied C2MS field to desired non-atrial tissue.

In some embodiments of the invention, one lead is placed in an atria and one lead is placed in a ventricle. And both are used to apply C2MS, or C2MS is applied between the two leads.

In some embodiments of the invention, the amplitude of a C2MS signal is selected based on the cardiac cycle. For example, if a C2MS signal is applied in atria not during a ventricular absolute refractory period, the amplitude may be reduced (or electrode location selected) so no dangerous levels of electrification reach the ventricle. At ventricular refractory times and/or when stimulating from the ventricle at a correct timing, a higher amplitude (e.g., voltage) may be used, even if it "covers" both part of an atria and part of a ventricle. For example, as noted above, inducing arrhythmia in the atria may not be an issue in arrhythmic patients and/or is less life threatening than when the ventricle is so stimulated.

In some embodiments of the invention, both C2MS and CRT are applied to the same patient. While such dual application may share electrodes (e.g., the left ventricular electrodes and/or the right ventricular electrodes, in some embodiments of the invention, an atrial electrode is used to apply C2MS (optionally with parameters that provide meaningful stimulation to the ventricle).

In some embodiments of the invention, the C2MS is used to treat and/or prevent AA. Optionally or additionally, the C2MS is used in addition or instead to treat the ventricle for heart failure. This last may be applied in hearts without AA.

In some embodiments of the invention, sensing in the atria (or other parts of the heart and/or rest of body) are used to estimate a level of AA, for example, the existence of an acute episode of AA and/or a general prevalence of AA. The treatment may be modified accordingly, for example, an atrial electrode (or an electrode nearer the atria) activated and/or a ventricular electrode activated at a higher amplitude in response to an acute and/or chronic increase in AA.

Some Results from Dogs

In a set of experiments, two healthy dogs were treated with C2MS and it was discovered that C2MS applied to the ventricular septum potentially reduces AA and/or susceptibility to AA.

In more detail, two dogs were put on rapid pacing of the atria to induce AF (by imitating an AA). Such induction was easy to achieve. The dogs maintained AF even after such rapid pacing was stopped, for example, for at least 10 min.

It is noted that in a typical heart, repeated sustained bouts of AF tend to increase the propensity of the heart to spontaneously develop an AF event and/or start an AF even if such AF is induced.

When C2MS (in ventricle) was applied, the AF terminated, within a minute or less. This process of AF induction and stopping the AF using C2MS was repeated several times.

Once C2MS had been applied for several days (about a week, at 5 hours/day), AF could not be induced using rapid pacing. The attempts to induce AF were repeated several times at several delays from end of C2MS application, ranging between a minute and 3 hours (exact numbers are unavailable). Such attempts failed on both animals and after multiple attempts at multiple times. Manual injection of a dog with a pro-arrhythmic drug in an amount expected to increase sensitivity of the atria to arrhythmic triggers also did not allow AF to be initiated by rapid pacing.

In general, it was found that before turning on C2MS treatment, AF could be induced by rapid atrial pacing. However, C2MS activation quite quickly caused reversion to NSR (normal sinus rhythm). After the animals had received C2MS for a few hours or weeks they were simply not inducible although they were under the same conditions (anesthetized and rapid pacing), even when pro-arrhythmic drugs were given.

In some embodiments of the invention, C2MS therapy is used to help reduce AA episodes, for example, by being applied for a period of, for example, 20 min, 40 min, 1 hour, 2 hours or intermediate or greater periods. On an acute basis (e.g., if an AA episode is detected), C2MS may be applied, for example, for 1 second, 10 seconds, 1 minute, 10 minutes, 20 minutes or intermediate or greater periods of time, optionally with some type of anti-arrhythmia pacing.

It is noted that a higher power level and/or more sensed electrodes can be used for acute treatment, as patient may be willing to accept a temporary discomfort if treatment is acutely needed. It is also noted that while power drain may increase with signal amplitude, for an acute therapy (e.g., less than 20%, 10%, 5% or intermediate percentages of applied beats, per day), this may be less of a consideration.

Optionally, the C2MS is applied to the ventricular septum. Optionally or additionally, the C2MS is applied to the atrium.

In some embodiments of the invention, C2MS is applied before and/or after an AA episode begins.

In some embodiments of the invention, certain physiological parameters are used to decide on application of C2MS, for example, increased heart rate or exercise and/or based on a timing of taking of anti-arrhythmic medication. Such application of C2MS may reduce a risk of an AA episode being triggered by these or other pro-arrhythmic conditions In some embodiments of the invention, C2MS is applied as a prophylactic treatment according to a schedule, for example, between 1 and 20 minutes every hour. Such treatment may be scheduled to cover the entire 24 hour period, for example, to prevent AF form happening at "off" times.

In some embodiments of the invention, C2MS is applied after an AA episode is treated (e.g., by cardioversion), for example, for between 1 and 120 minutes, for example, between 5 and 60 minutes, potentially maintaining the non-arrhythmic condition, especially in the face of pro-arrhythmic conditions caused by the treated AA episode and/or treatment thereof.

In some embodiments of the invention, C2MS is applied for similar ranges of time, to prevent AF after defibrillation is applied, for example, to prevent AA from occurring. In a more general sense, in some embodiments of the invention, upon detection or estimation of increasing level of atrial arrhythmogenicity, device 200 is used to provide C2MS to suppress such arrhythmogenicity.

When applying C2MS after a treatment, C2MS application start is optionally delayed, for example, for between 1 and 300 seconds or between 30 and 200 seconds or intermediate or greater delays.

By "applying C2MS for XX minutes", what is meant is that the controller logic is set to apply a C2MS signal every beat (or possibly according to another schedule, such as every other beat), for the period of time, however, it is noted that some beats will not be treated, for example, due to ventricular activation irregularity.

In some embodiments of the invention, the heart rate limit (above which no C2MS is applied) is increased.

Exemplary AF Patient Selection and Treatment

Figure 8:
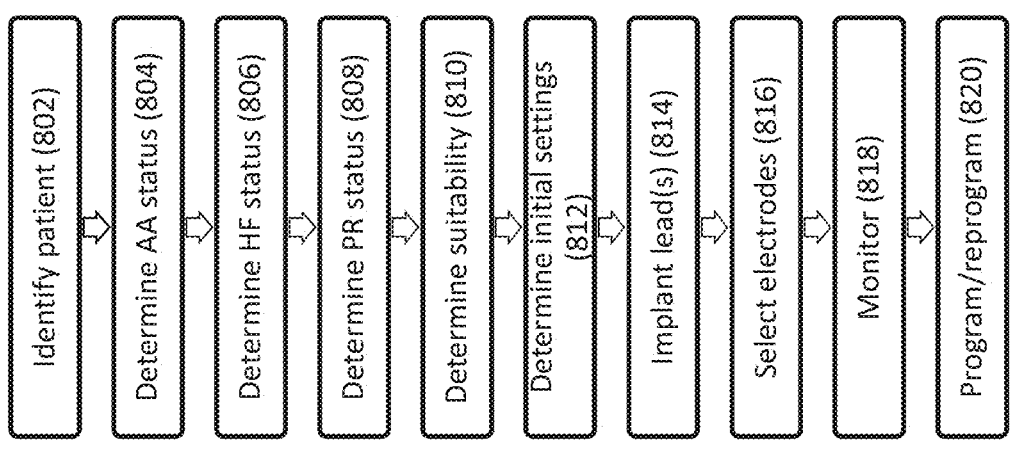
FIG. 8 is a flowchart of a method of patient selection and treatment for patients with atrial arrhythmia issues, in accordance with some embodiments of the invention.

FIG. 8 is a flowchart of a method of patient selection and treatment for patients with atrial arrhythmia issues, in accordance with some embodiments of the invention, noting that the acts described can be performed in parallel and/or in other orders, in some embodiments.

At 802 a patient with a cardiac condition and potential for benefit from a treatment, for example, as described herein is identified. For example, a heart failure patient at NYAH stage II (or higher), optionally with AF may be identified. For example, such a patient may be selected to have an ejection fraction (EF) of between 20% and 50%, for example, between 25% and 40% or 45%. Optionally or additionally, such patient may have chronic angina (e.g., angina pectoris). Optionally or additionally, such a patient may have a 6 min walk test of less than 800 meters, 600 meters, 400 meters and/or intermediate values. In some embodiments of the invention, the patient has a significant pulmonary reserve, for example, expected to allow increase of flow of oxygenated blood by between, for example, 5%-20%, 20%-40%, 40%-60%, 60%-100%, 100%-200% and/or intermediate or greater percentages relative to rest in the patient (cardiac output permitting). In some embodiments of the invention, the patient has a Peak VO2 of between 8 and 20 ml O2/min/Kg.

In some embodiments of the invention, a patient is selected based on an amount of treatable beats. For example, a patient where at least 20%, 40%, 50%, 80% or intermediate percentages of his heart beats can be treated using C2MS when considering safety of the patient.

At 804, the status of atrial arrhythmia of the patient is optionally determined, for example, a patient can be identified as having paroxysmal AF. It is noted that in some embodiments patients that do not have AF, but may have a risk of developing AF (e.g., having sleep apnea), are selected. In some embodiments of the invention, the patient spends between 0% and 10% of the time (e.g., average over a month) in AA, between 10% and 30% in AA, between 30% and 50% in AA or above 50%, possibly up to 90% or 100% in AA. Increased percentage may indicate increased severity of AA. In some embodiments of the invention, the patient has an estimated risk (e.g., using clinical and/or diagnostic methods known in the art) of developing an AA such as, for example episodic AF or progressing to chronic AF in the upcoming 1 year of 5%, 10%, 20%, 30%, 50%, 70% or intermediate or greater risk levels.

At 806, a heart failure state of the patient is optionally determined. Optionally, a HF state is defined according to a lower than desired cardiac output. It is noted that in some embodiments patients that do not have significant heart failure (e.g., NYHA stage I and/or below) are treated. In other embodiments, patients with acceptable resting behavior (e.g., NYHA II or II) are treated. In some embodiments of the invention, patients with NYAH IV are treated.

At 808, a pulmonary reserve status is optionally determined. In some cases, C2MS treatment is provided independently of respiratory status and/or availability of respiratory reserve.

At 810 suitability of a patient for treatment is determined, for example, based on expected improvement, based on existence of disease that can be treated and/or based on a desired prophylactic effect and/or based on an expected cardiac response (e.g., number of expected treated beats). In particular it is noted that a patient may be selected because the patient has atrial fibrillation (or other AA) or in spite of such AA.

At 812, initial stimulation settings are optionally determined, for example, desired lead location, tissue to be affected by C2MS (and hence signal amplitude and/or timing) and/or application logic.

In some embodiments of the invention, a combination of timing and amplitude are used to determine which tissue will be in range of a signal form the lead, at what time and for how long.

Planning may include setting desired ranges for such values and running a simulation or other solver to determine signal application parameters which meet the requirements.

At 814, one or more leads are implanted in and/or near the heart, for example, in a right atrium and/or a right ventricle. Optionally, existing leads (e.g., of a pacemaker and/or a defibrillator) are reused or used in parallel for C2MS application.

In some embodiments of the invention, the lead locations (e.g., non-septal) are selected to reduce electrification of, for example, nerves or nerve plexuses in the heart or outside the heart and/or reduce stimulation of other thoracic tissue.

In some embodiments of the invention, the electrodes are external leads or other non-implanted leads, for example, electrode(s) on a catheter, for example, to be used for a short treatment, for example cardioversion. Optionally, the electrification is via a needle which is used to penetrate through the skin and other outer layers of the body.

At 816, electrodes to be stimulated are optionally selected.

At 818, the effect of initial signal parameters is optionally monitored.

At 820, the application parameters and/or logic are optionally programmed and/or reprogrammed (e.g., in response to such monitoring), for example, using an external controller.

It is noted that such a method as described herein may include a therapy planning stage (e.g., up to 812, 88, 820) and followed by a treatment phase (e.g., 814, 816), one of which is optionally omitted.

Exemplary Non-AF Patient Selection and/or Treatment

Figure 9:
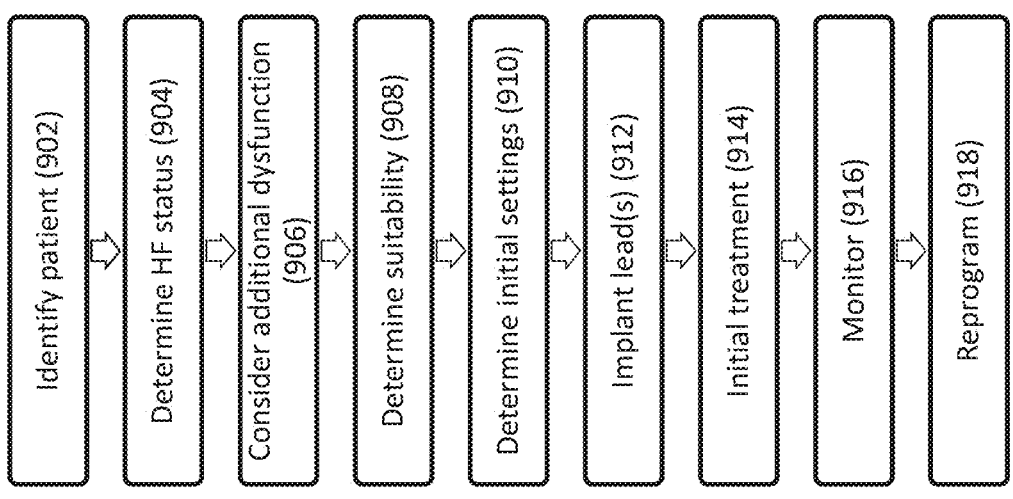
FIG. 9 is a flowchart of a method of patient selection and treatment for patients with cardiac out and an additional cardiac dysfunction, in accordance with some embodiments of the invention.

FIG. 9 is a flowchart of a method of patient selection and treatment planning and optional carrying out of treatment for patients with cardiac output and an additional cardiac dysfunction, in accordance with some embodiments of the invention. In some embodiments of the invention, both dysfunctions are treated using a same C2MS signal.

At 902 a patient who has heart failure and/or an AA, and an additional existing or potential cardiac dysfunction is considered.

At 904, the status of heart failure and/or AA is determined, for example, as described with reference to FIG. 8.

At 906, the additional (one or more) dysfunction is determined. Example dysfunctions include: HOCM, an implant such as a valve (e.g., mitral, aortic, tricuspid), a clip (e.g., mitral or tricuspid), diseased tissue and/or weakened tissue, such dysfunction may be existing (e.g., diseased cardiac tissue) or potential (e.g., a clip not yet implanted).

At 910, initial settings for C2MS treatment are determined. In some embodiments of the invention, such settings are selected to provide a tradeoff between maximizing a therapeutic effect on one dysfunction and maximizing a therapeutic effect for the other dysfunction. For example, a lead location may be selected which provides less cardiac output enhancement but, at the same time provide a satisfactory level of AF prevention/treatment and/or avoids stimulating diseased or sick tissue and/or reduced mechanical problems in the heart.

At 912, one or more leads are optionally implanted in the heart.

At 914, treatment is started, optionally after an implant.

At 916, effects of such treatment are monitored.

At 918, stimulation parameters are optionally reset.

Exemplary Operation of Implant

Figure 10:
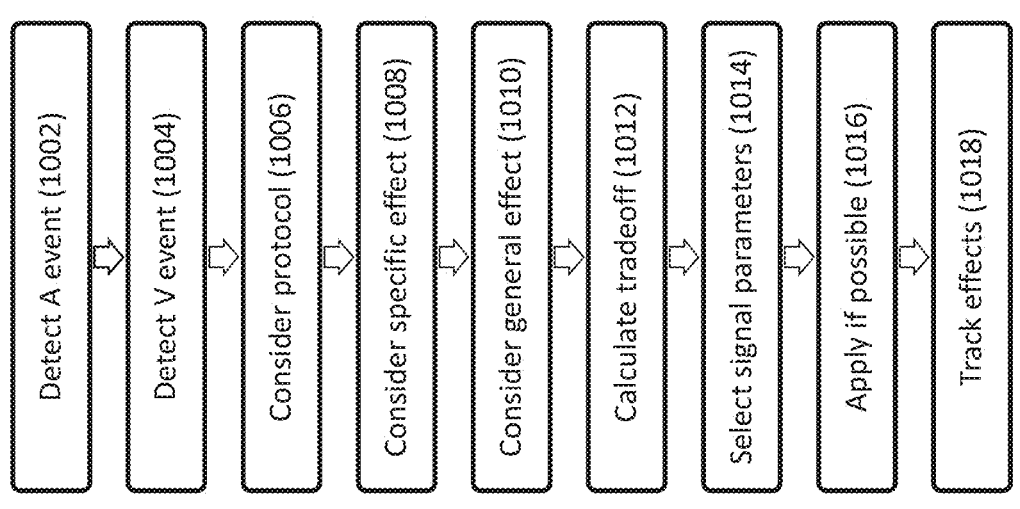
FIG. 10 is a flowchart of operation of a cardiac controller, in accordance with some embodiments of the invention.

FIG. 10 is a flowchart of operation of a cardiac therapy device (e.g., device 200), in accordance with some embodiments of the invention.

At 1002, an atrial event (e.g., start of activation or existence of arrhythmia) is optionally detected.

At 1004, a ventricular event (e.g., start of activation or existence of arrhythmia is optionally detected.

These detected events are optionally used as input for one or both of deciding that therapy to apply and/or deciding if to apply therapy. In some embodiments of the invention, the order is opposite form the order shown here—first a decision as to potential therapies is performed and then detection (if any) of one or more events is carried out.

At 1006, the protocol being used is optionally considered (e.g., selected from a set or calculated), for example "apply C2MS for 7 hours" or "apply C2MS in response to AF" or "apply C2MS to change cardiac activation so HOCM is less likely to obstruct aortic outlet", each of which is an exemplary possible application protocol.

At 1008, a specific desired effect is optionally considered, for example, a reduction in AA. This can be, for example, if 1002 detected an atrial arrhythmia or if an acute need in increasing cardiac output is detected.

At 1010, a general effect is optionally considered, for example, providing a general dosage of C2MS to reverse fetal gene program.

At 1012, tradeoffs between the various effects are considered, for example, selecting application parameters that treat AF, at the expense of a lesser improvement in cardiac output.

At 1014, signal parameters which achieve such tradeoff are select. It is noted that in some cases, such parameters are selected before or with the tradeoffs. In some embodiments of the invention, such parameters are selected based on what can be expected to be applicable to the heart at a current or a near beat.

At 1016, optionally in response to passing safety test, the signal is applied to the heart.

At 1018, an effect of the applying is monitored and may change the goals and/or protocol used for later applications. For example, if a signal is not sufficient to stop AF, an increase in signal may be used (e.g., up to a threshold parameter value).

General

It is expected that during the life of a patent maturing from this application many relevant non-excitatory cardiac treatments will be developed; the scope of the term non-excitatory is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A cardiac treatment device, comprising:
a stimulation circuitry configured to:
   generate a non-excitatory electrical signal, wherein when said signal is configured to be applied to a ventricular tissue during a ventricular refractory period it improves a condition of heart failure in human patients;
an atrial arrhythmia detection circuitry; and
a decision circuitry which controls the stimulation circuitry to deliver said signal during said ventricular refractory period, both when said atrial arrhythmia detection circuitry detects an atrial arrhythmia and when said atrial arrhythmia detection circuitry does not detect said atrial arrhythmia.

2. A device according to claim 1, wherein said decision circuitry controls modification of at least one parameter of said signal delivered by said stimulation circuitry in response to a detection of said atrial arrhythmia.

3. A device according to claim 2, wherein said modification comprises increasing a spatial range of tissue stimulated by said signal.

4. A device according to claim 3, wherein tissue configured to be stimulated by said signal comprises one or more of ventricular septum, right atrium, left atrium, AV node or pulmonary vein's junction with left atria.

5. A device according to claim 1, wherein said decision circuitry is configured to avoid said delivery if a ventricular arrhythmia is detected.

6. A device according to claim 1, wherein said decision circuitry is configured to allow said delivery if a supraventricular arrhythmia is detected.

7. A device according to claim 1, wherein said device includes a memory with an indication of a dosage of said signal to be applied and a time duration of application and wherein said decision circuitry is configured to modify an actual duration of signal application according to an actual delivery of signals.

8. A device according to claim 1, wherein said device is configured to apply said signal also during a non-refractory time in an atria of said patient.

9. A device according to claim 1, wherein said device has no atrial leads.

10. A device according to claim 1, wherein said device includes pacing circuitry and wherein said decision circuitry is programmable to selectively prefer applying a non-excitatory signal over applying an increase in pacing in cases of increased cardiac demand.

11. A device according to claim 1, wherein said atrial arrhythmia detection circuitry detects atrial arrhythmia from signals measured by one or more ventricular leads.

12. A device according to claim 1, wherein said device has no ventricular stimulation leads.

13. The cardiac treatment device of claim 1, wherein said non-excitatory electrical signal is configured to be delivered using different parameters when said atrial arrhythmia detection circuitry detects said atrial arrhythmia as compared to when said atrial arrhythmia detection circuitry does not detect said atrial arrhythmia.

14. A cardiac treatment device, comprising:
a stimulation circuitry configured to:
   generate a non-excitatory electrical signal, wherein when said signal is configured to be applied to a ventricular tissue during a ventricular refractory period it improves a condition of heart failure in human patients;
an atrial arrhythmia detection circuitry; and
a decision circuitry which controls the stimulation circuitry to deliver said signal during said ventricular refractory period regardless of detection of presence or absence of said atrial arrhythmia by said atrial arrhythmia detection circuitry.

15. A cardiac treatment device, comprising:
a stimulation circuitry configured to:
generate a non-excitatory electrical signal, wherein when said signal is configured to be applied to a ventricular tissue during a ventricular refractory period it improves a condition of heart failure in human patients;
an atrial arrhythmia detection circuitry;
a memory with a treatment protocol to deliver said non-excitatory electrical signal according to a schedule, and
a decision circuitry which controls the stimulation circuitry to deliver said treatment during said ventricular refractory period, both when said atrial arrhythmia detection circuitry detects an atrial arrhythmia and when said atrial arrythmia detection circuitry does not detect said atrial arrhythmia.

16. A method of planning treatment for a patient, comprising:
(a) identifying that a patient has an atrial arrhythmia or a risk to develop thereof; and
(b) planning and implementing a treatment schedule for the patient with an implanted device that generates a non-excitatory electrical signal which, when applied to ventricular tissue during a ventricular refractory period thereof improves a condition of heart failure in human patients, wherein said non-excitatory electrical signal is applied both during an atrial arrhythmia event and in the absence of said atrial arrhythmia event.

17. A method according to claim 16, wherein said non-excitatory electrical signal is applied during said atrial arrhythmia event with different parameters than when applied in the absence of said atrial arrhythmia event.

18. A method according to claim 16, comprising selecting said patient and performing said planning with a goal of improving a symptom of said atrial arrhythmia by said treating.

19. A method according to claim 16, wherein said improving comprises preventing abnormal ventricular activation by said atrial arrhythmia.

20. A method according to claim 16, wherein said improving comprising reducing said atrial arrhythmia.

21. A method according to claim 16, wherein said planning comprises planning to apply said non-excitatory signal within 20 mm from a ventricular septum.

22. A method according to claim 16, wherein said planning comprises planning to apply said non-excitatory signal within an atrium of the heart.

23. A method according to claim 16, wherein said planning comprises selecting a power level and an application location to stimulate cardiac tissue in both an atria and a ventricle.

24. A method according to claim 16, wherein said identifying comprises selecting for treatment patients with episodic AF or patients with chronic AF.

25. A method according to claim 24, wherein said identifying comprises selecting for treatment patients at risk of developing an AA, above 20% in the next year.

26. A method according to claim 24, wherein said identifying comprises selecting for treatment patients where at least 50% of beats are treatable using said device when considering safety of the patient.

27. A method according to claim 16, wherein said planning comprises planning with a goal to reduce AF episodes in said patient.

28. A method according to claim 16, wherein said planning comprises programming the device to apply said signal during a portion of the ventricular refractory period late enough so that said refractory period is extended.

29. A method according to claim 16, wherein said planning comprises setting up device parameters to apply said signal to above 20,000 treated beats per day, on the average for a month.

30. The method of claim 16, wherein said non-excitatory electrical signal is delivered using different parameters when applied during the atrial arrhythmia event as compared to when applied in the absence of said atrial arrhythmia event.

31. A method of planning treatment for a patient, comprising:
   (a) identifying that a patient has an atrial arrhythmia or a risk to develop thereof; and
   (b) planning and implementing a treatment schedule for the patient with an implanted device that generates a non-excitatory electrical signal which, when applied to ventricular tissue during a ventricular refractory period thereof improves a condition of heart failure in human patients, wherein said non-excitatory electrical signal is applied regardless of detection of presence or absence of an event of said atrial arrhythmia.

32. A method of planning treatment for a patient, comprising:
   (a) identifying that a patient has an atrial arrhythmia or a risk to develop thereof; and
   (b) planning and implementing a treatment schedule for the patient with an implanted device that generates a non-excitatory electrical signal which, when applied to ventricular tissue during a ventricular refractory period thereof improves a condition of heart failure in human patients, wherein said treatment schedule is a prophylactic treatment according to a schedule, wherein said non-excitatory electrical signal is applied according to said prophylactic treatment schedule, wherein the non-excitatory electrical signal is applied both during an atrial arrhythmia event and in the absence of said atrial arrhythmia event.

* * * * *